(12) United States Patent
Vidal et al.

(10) Patent No.: US 7,060,110 B2
(45) Date of Patent: Jun. 13, 2006

(54) DYEING COMPOSITION FOR DYEING KERATINOUS FIBRES COMPRISING A PARTICULAR DICATIONIC MONOAZO DYE

(75) Inventors: Laurent Vidal, Paris (FR); Hervé David, Joinville le Pont (FR)

(73) Assignee: L'Oreal, Paris (FR)

( * ) Notice: Subject to any disclaimer, the term of this patent is extended or adjusted under 35 U.S.C. 154(b) by 178 days.

(21) Appl. No.: 10/473,810

(22) PCT Filed: Apr. 3, 2002

(86) PCT No.: PCT/FR02/01153

§ 371 (c)(1),
(2), (4) Date: Dec. 11, 2003

(87) PCT Pub. No.: WO02/080869

PCT Pub. Date: Oct. 17, 2002

(65) Prior Publication Data

US 2004/0093676 A1 May 20, 2004

(30) Foreign Application Priority Data

Apr. 3, 2001 (FR) .......................................... 01 04537

(51) Int. Cl.
*A61K 7/13* (2006.01)

(52) U.S. Cl. ........................ 8/405; 8/407; 8/565; 8/567; 8/568; 8/570; 8/571; 8/572; 8/573; 8/574; 8/654; 8/655; 546/184; 548/318.1; 548/400

(58) Field of Classification Search ................... 8/405, 8/407, 565, 567, 568, 570, 571, 572, 573, 8/574, 654, 655; 546/184; 548/318.1, 400
See application file for complete search history.

(56) References Cited

U.S. PATENT DOCUMENTS

| | | | |
|---|---|---|---|
| 3,578,386 A | 5/1971 | Kalopissis et al. ............... 8/10 |
| 3,578,387 A | 5/1971 | Zviak et al. .................. 8/10.1 |
| 3,649,162 A | 3/1972 | James .............................. 8/41 |
| 4,003,699 A | 1/1977 | Rose et al. .................... 8/10.2 |
| 5,061,289 A | 10/1991 | Clausen et al. ................ 8/405 |
| 5,380,340 A | 1/1995 | Neunhoeffer et al. .......... 8/409 |
| 5,708,151 A | 1/1998 | Möckli ....................... 534/608 |
| 5,766,576 A | 6/1998 | Löwe et al. .................. 429/62 |
| 5,852,179 A | 12/1998 | Dado ......................... 534/581 |
| 5,879,412 A | * 3/1999 | Rondeau et al. ............... 8/411 |
| 6,099,592 A | 8/2000 | Vidal et al. .................... 8/409 |
| 6,099,593 A | 8/2000 | Terranova et al. ............. 8/409 |
| 2001/0001333 A1 | 5/2001 | Samain .......................... 8/426 |
| 2002/0002748 A1 | 1/2002 | Rondeau ........................ 8/405 |

FOREIGN PATENT DOCUMENTS

| | | |
|---|---|---|
| DE | 23 59 399 | 6/1975 |
| DE | 28 22 912 | 11/1979 |
| DE | 38 43 892 | 6/1990 |
| DE | 41 28 490 | 3/1993 |
| DE | 41 33 957 | 4/1993 |
| DE | 195 43 988 | 5/1997 |
| DE | 197 21 619 | 11/1998 |
| EP | 0 714 954 | 6/1996 |
| EP | 0 770 375 | 5/1997 |
| EP | 0 962 219 | 12/1999 |
| FR | 1 584 965 | 1/1970 |
| FR | 2 733 749 | 11/1996 |
| FR | 2 741 798 | 6/1997 |
| FR | 2 750 048 | 12/1997 |
| GB | 1 026 978 | 4/1966 |
| GB | 1 153 196 | 5/1969 |
| GB | 2 028 856 | 3/1980 |
| GB | 2 070 050 | 9/1981 |
| JP | 55-22638 | 2/1980 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 96/15765 | 5/1996 |

OTHER PUBLICATIONS

Co–pending U.S. Appl. No. 10/473,628 (Dyeing composition for dyeing keratinous fibers comprising a cationic azo–dye, filed on Feb. 23, 2004.*

Mohammad Hossein Habibi et al., "Efficient Catalytic Oxidation of Primary Aromatic Amines to Azo Derivatives by Manganese (III) Tetraphenylporphyrin," J. Chem. Research, (S), 1998, pp. 648–649.

Xiao–Yang Wang et al., "The Preparation of Symmetrical Azobenzenes From Anilines by Phase Transfer Catalyzed Method," Synthetic Communications, vol. 29, No. 13, 1999, pp. 2271–2276.

Dawel Ma et al., "CuI–Catalyzed Coupling Reaction of β–Amino Acids or Esters with Aryl Halides at Temperature Lower Than That Employed in the Normal Ullmann Reaction. Facile Synthesis of SB–214857," Organic Letters, vol. 3, No. 16, 2001, pp. 2583–2586.

Kevin H. Shaughnessy et al., "Sterically Demanding, Water-Soluble Alkylphosphines as Ligands for High Activity Suzuki Coupling of Aryl Bromides in Aqueous Solvents," Organic Letters, vol. 3, No. 17, 2001, pp. 2757–2759.

Christopher G. Frost et al., "Recent Developments in Aromatic Heteroatom Coupling Reactions," J. Chem. Soc., Perkin Trans. 1, No. 16, Aug. 21, 1998, pp. 2615–2623.

English language Derwent Abstract of DE 28 22 912, Nov. 28, 1979.

English language Derwent Abstract of DE 41 28 490, Mar. 4, 1993.

(Continued)

*Primary Examiner*—Eisa Elhilo
(74) *Attorney, Agent, or Firm*—Finnegan Henderson Farabow Garrett & Dunner, L.L.P.

(57) ABSTRACT

The invention concerns a novel dyeing composition for dying keratinous fibers, in particular human hair, comprising a dicationic monoazo dye, and the dyeing method using said composition and the novel compounds of formulae (I) or (II).

40 Claims, No Drawings

OTHER PUBLICATIONS

English language Derwent Abstract of DE 197 21 619, Nov. 26, 1998.

English language Derwent Abstract of EP 0 770 375, May 2, 1997.

English language Derwent Abstract of JP 55-22638, Feb. 18, 1980.

English language Derwent Abstract of JP 2-19576, Jan. 23, 1990.

English language Derwent Abstract of JP 5-163124, Jun. 29, 1993.

* cited by examiner

DYEING COMPOSITION FOR DYEING KERATINOUS FIBRES COMPRISING A PARTICULAR DICATIONIC MONOAZO DYE

A subject matter of the invention is a novel dyeing composition for the dyeing of keratinous fibers, in particular of human hair, comprising a specific dicationic monoazo dye and the process for dyeing keratinous fibers employing such a composition. Another subject matter of the invention is novel monocationic diazo dyes.

It is known to dye keratinous fibers and in particular human hair with dyeing compositions comprising oxidation dye precursors, generally known as oxidation bases, such as ortho- or para-phenylenediamines, ortho- or para-aminophenols and heterocyclic compounds. These oxidation bases are colorless or weakly colored compounds which, in combination with oxidizing substances, give rise to colored compounds by an oxidative coupling process.

It is also known that the hues obtained with these oxidation bases can be varied by combining them with couplers or coloring modifiers, the latter being chosen in particular from aromatic meta-diamines, meta-aminophenols meta-diphenols and certain heterocyclic compounds, such as indole compounds.

The variety of the molecules employed as oxidation bases and couplers makes it possible to obtain a rich palette of colors.

This oxidation dyeing process consists in applying, to the keratinous fibers, oxidation bases or a mixture of oxidation bases and of couplers with an oxidizing agent, for example aqueous hydrogen peroxide solution, in leaving to stand and in then rinsing the fibers. The colorations which result therefrom are permanent and powerful, and withstand external agents, in particular light, bad weather, washing, perspiration and rubbing. Generally applied at basic pH, they make it possible to obtain dyeing and simultaneously lightening of the fiber, which is reflected in practice by the possibility of obtaining a final coloration which is lighter than the original color. In addition, lightening the fiber has the advantageous effect of producing a unified color in the case of gray hair and, in the case of naturally pigmented hair, of making the color emerge, that is to say of rendering it more visible.

It is also known to dye human keratinous fibers by direct dyeing. The process conventionally used in direct dyeing consists in applying, to the keratinous fibers, direct dyes, which are colored and coloring molecules having an affinity for the fibers, in leaving to stand and in then rinsing the fibers.

It is known, for example, to use nitrobenzene, anthraquinone or nitropyridine direct dyes, azo, xanthene, acridine or azine dyes or triarylmethane dyes.

The colorations which result therefrom are particularly chromatic colorations which, however, are temporary or semipermanent because the nature of the interactions which bind the direct dyes to the keratinous fiber and their desorption from the surface and/or from the core of the fiber are responsible for their low dyeing power and for their poor resistance to washing or to perspiration. In addition, these direct dyes are generally sensitive to light, because of the low resistance of the chromophore with regard to photochemical attacks, and result over time in fading of the coloring of the hair. In addition, their sensitivity to light is dependent on their distribution, uniform or nonuniform, in the keratinous fiber.

It is known to use direct dyes in combination with oxidizing agents. However, direct dyes are generally sensitive to the action of oxidizing agents, such as aqueous hydrogen peroxide solution, and reducing agents, such as sodium bisulfite, which generally renders them difficult to use in compositions for lightening direct dyeing based on aqueous hydrogen peroxide solution and based on a basifying agent or in oxidation dyeing compositions in combination with oxidation dye precursors or couplers.

For example, provision has been made, in Patent Applications FR-1 584 965 and JP-062 711 435, to dye the hair with dyeing compositions based on direct nitro dyes and/or on disperse azo dyes and on aqueous ammoniacal hydrogen peroxide solution by applying, to the hair, a mixture of said dyes and of said oxidizing agent prepared immediately before use. However, the colorations obtained prove to be insufficiently persistent and disappear on shampooing, allowing the lightening of the hair fiber to become apparent. Such a coloration becomes unattractive on changing over time.

Provision has also been made, in Patent Applications JP-53 95693 and JP 55 022638, to dye the hair with compositions based on cationic direct dyes of oxazine type and on aqueous ammoniacal hydrogen peroxide solution by applying, to the hair, in a first stage, aqueous ammoniacal hydrogen peroxide solution and then, in a second stage, a composition based on the direct oxazine dye. This coloration is not satisfactory because of the fact that it requires a process rendered excessively slow by the leave-in times of the two successive stages. Furthermore, if a mixture prepared at the time of use of the direct oxazine dye with aqueous ammoniacal hydrogen peroxide solution is applied to the hair, no coloration is produced or, at least, a coloration of the hair fiber is obtained which is virtually nonexistent.

More recently, Patent Application FR 2 741 798 has disclosed dyeing compositions comprising direct azo or azomethine dyes comprising at least one quaternized nitrogen atom, said compositions having to be mixed at the time of use at basic pH with an oxidizing composition. These compositions make it possible to obtain colorations with homogeneous, persistent and bright highlights. However, they do not make it possible to dye keratinous fibers with as much power as with oxidation dyeing compositions.

There thus exists a real need to try to find chromatic direct dyes which make it possible to dye keratinous fibers as powerfully as oxidation dyes, which are as stable as them toward light and are also resistant to bad weather, washing and perspiration, and which, in addition, are sufficiently stable in the presence of oxidizing and reducing agents to be able to simultaneously obtain lightening of the fiber, either by use of lightening direct compositions comprising them or by the use of oxidation dyeing compositions comprising them. There also exists a real need to try to find direct dyes which make it possible to dye keratinous fibers in order to obtain a very broad range of colors, in particular highly chromatic colors, without forgetting the "basic" shades, such as the blacks and the browns.

These aims are achieved with the present invention, a subject matter of which is a composition for dyeing keratinous fibers, and in particular human keratinous fibers such as the hair, comprising at least one dicationic monoazo dye of the following formulae (I) or (II):

in which formulae n is equal to 0 or 1, $Z_1$ represents a 5- or 6-membered cationic heteroaromatic radical of formulae (III) or (IV):

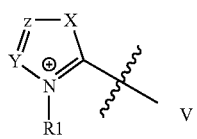

(III)

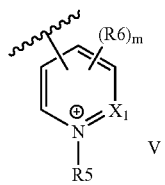

(IV)

where
X represents $NR_3$, S or O, Z represents $CR_2$ or N and Y represents $CR_4$ or N with the following conditions:
when X is $NR_3$ or O and Z is $CR_2$, then Y is $CR_4$ or N,
when X is S, then Z is N or Y is N
when X is S and Z is N, then Y is $CR_4$
$X_1$ represents $CR_6$ or N,
m is an integer equal to 0, 1, 2 or 3,
$R_1$, $R_3$ and $R_5$ represent, independently of one another, a linear or branched, saturated or unsaturated $C_1$–$C_{10}$ hydrocarbonaceous chain which can form an optionally aromatic, 5- to 7-membered carbonaceous ring; it being possible for one or more carbon atoms to be replaced by an oxygen, nitrogen, halogen or sulfur atom or by an $SO_2$ group, with the exception of the carbon connected to the nitrogen atom of the ring of formula (III) or (IV); the radicals $R_1$, $R_3$ or $R_5$ not comprising a peroxide bond or diazo, nitro or nitroso radicals;
$R_2$, $R_4$ and $R_6$ represent, independently of one another, a hydrogen atom; a linear or branched, saturated or unsaturated $C_1$–$C_{10}$ hydrocarbonaceous chain which can form an optionally aromatic 5- to 7-membered carbonaceous ring; it being possible for one or more carbon atoms to be replaced by one or more oxygen, nitrogen or sulfur atoms, or by an $SO_2$ group; the radicals $R_2$, $R_4$ or $R_6$ not comprising a peroxide bond or diazo, nitro or nitroso radicals; the radicals $R_2$ and $R_4$ can form together a carbonaceous aromatic ring,
V represents an organic or inorganic anion,
$A_1$ and $A_3$ represent, independently of one another, a divalent radical of formulae (V) or (VI)

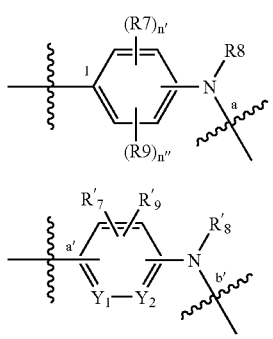

(V)

(VI)

in which
n' is an integer equal to 0, 1, 2 or 3,
n" is an integer equal to 0 or 1, $Y_1$–$Y_2$ represents C—N or N—N,
when n=0, then the bond a of the group $A_1$ of formula (V) is connected to the functional group $Z_2$ Of formula (I) or,
when n=0, then the bond b' of the group $A_1$ of formula (VI) is connected to the functional group $Z_2$ of formula (I),
when n=1, then the bond a of the group $A_1$ of formula (V) is connected to the $C_1$ of the group $A_3$ of formula (V), the bond a of the group $A_3$ of formula (V) being connected to the functional group $Z_2$ of formula (I) or,
when n=1, then the bond a of the group $A_1$ of formula (V) is connected to the carbon carrying the bond a' of the group $A_3$ of formula (VI), the bond b' being connected to the functional group $Z_2$ of formula (I),
when n=1, then the bond b' of the group $A_1$ of formula (VI) is connected to the $C_1$ carbon of the group $A_3$ of formula (V), the bond a being connected to the functional group $Z_2$ of formula (I) or,
when n=1, then the bond b' of the group $A_1$ of formula (VI) is connected to the carbon carrying the bond a' of the group $A_3$ of formula (VI), the bond b' of the group $A_3$ of formula (VI) being connected to the functional group $Z_2$ of formula (I),
$R_8$ and $R'_8$ represent, independently of one another, a noncationic group chosen from a hydrogen atom, a linear or branched $C_1$–$C_{10}$ hydrocarbonaceous chain which can form an optionally aromatic 5- to 7-membered carbon ring; it being possible for one or more carbon atoms of the hydrocarbonaceous chain to be replaced by one or more oxygen, nitrogen or sulfur atoms, or by an $SO_2$ group with the exception of the carbon connected to the nitrogen atom; the radicals $R_8$ or $R'_8$ not comprising a peroxide bond or diazo, nitro or nitroso radicals;
$R_7$, $R_9$, $R'_7$ and $R'_9$ represent, independently of one another, a noncationic group as defined for $R_2$ or a cationic group $Z_3$, provided that only one of the groups $R_7$, $R_9$, $R'_7$ and $R'_9$ is cationic,
$R_7$ with $R_8$, respectively $R'_7$ with $R'_8$ can form together a saturated 5- or 6-membered heterocycle,
$Z_3$ is a cationic group represented by the following formula (VII)

—(B)$_{n'''}$—D    (VII)

in which:
B represents a linear or branched hydrocarbonaceous chain comprising from 1 to 15 carbon atoms, which can form one or more optionally aromatic 3- to 7-membered rings, and one or more carbon atoms of which can be replaced by an oxygen, nitrogen or sulfur atom, or by an $SO_2$ radical, with the exception of the carbon connected to the nitrogen atom; B not comprising a peroxide bond or diazo, nitro or nitroso radicals,
the radical B is connected to D by any of the atoms of the radical D,
n''' can take the value 0 or 1,
D is chosen from the cationic groups of the following formulae (VIII) and (IX):

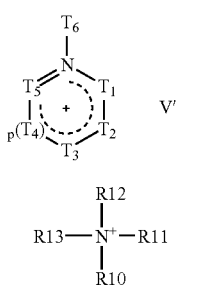 (VIII)

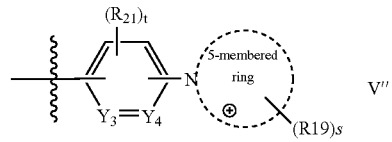 (IX)

in which:
p can take the value 0 or 1;
$T_1$, $T_2$, $T_3$ and $T_4$, independently of one another, represent an oxygen atom; a sulfur atom; a nitrogen atom which is unsubstituted or substituted by a radical $R_{14}$; or a carbon atom which is unsubstituted or substituted by one or two identical or different radicals $R_{14}$;
$T_5$ represents a nitrogen atom; or a carbon atom which is unsubstituted or substituted by a radical $R_{14}$;
$T_6$ can have the same meanings as those indicated below for the radical $R_{14}$, it being understood that $T_6$ is different from a hydrogen atom;
$T_1$ or $T_5$ can additionally form with $T_6$ a 5- to 7-membered saturated or unsaturated ring, each member being unsubstituted or substituted by one or two identical or different radicals $R_{14}$;
two of the adjacent radicals $T_1$, $T_2$, $T_3$, $T_4$ and $T_5$ can additionally form a 5- to 7-membered ring, each member being independently represented by a carbon atom which is unsubstituted or substituted by one or two identical or different radicals $R_{14}$, a nitrogen atom which is unsubstituted or substituted by a radical $R_{14}$, an oxygen atom or a sulfur atom;
$R_{10}$, $R_{11}$, $R_{12}$, $R_{13}$ and $R_{14}$, which are identical or different, represent a hydrogen atom; a linear or branched hydrocarbonaceous chain comprising from 1 to 10 carbon atoms, which are optionally aromatic, and one or more carbon atoms of which can be replaced by an oxygen, nitrogen or sulfur atom, or by an $SO_2$ group, and one or more carbon atoms of which can, independently of one another, be substituted by one or more halogen atoms; said radical not comprising a peroxide bond or diazo, nitro or nitroso radicals;
$R_{10}$, $R_{11}$ and $R_{12}$ can also form, in pairs with the quaternary nitrogen atom to which they are attached, one or more 5- to 7-membered saturated rings, each member being independently represented by a carbon atom which is unsubstituted or substituted by one or two identical or different radicals $R_{14}$, a nitrogen atom which is unsubstituted or substituted by a radical $R_{14}$, an oxygen atom, or a sulfur atom;
when n'''=0, then the group of formula (IX) can be connected to the compound of formula (V) and (VI) directly by the nitrogen atom of the quaternary ammonium, $R_{13}$ representing in this case a single bond,
V' represents an organic or inorganic anion,
$Z_2$ represents a linear or branched $C_1$–$C_{10}$ hydrocarbonaceous chain which can form an optionally aromatic 5- to 7-membered carbonaceous ring; it being possible for one or more carbon atoms to be replaced by one or more oxygen, nitrogen or sulfur atoms, or by an $SO_2$ group, said radical $Z_2$ not comprising a peroxide bond or diazo, nitro or nitroso radicals; a cationic group $Z_3$ as defined above, with the proviso that $Z_2$ is not cationic when $R_7$, $R_9$, $R'_7$ or $R'_9$ is cationic, $A_2$ represents a radical of formula (X) corresponding to a carbonaceous aromatic, pyridine or pyridazine radical substituted by a 5-membered cationic heteroaromatic radical, optionally substituted by one or more radicals $R_{19}$ having the same definition as $R_2$; a radical of formula (XI)

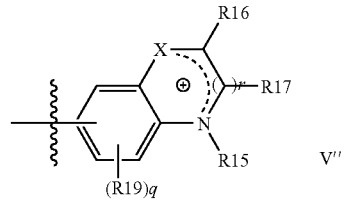 (X)

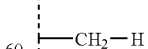 (XI)

in which
r is an integer equal to 0 or 1,
q is an integer equal to 0, 1, 2 or 3,
s is an integer equal to 0, 1, 2, 3, 4 or 5,
t is an integer equal to 0, 1 or 2,
$Y_3=Y_4$ represents C═C, C═N or N═N,
if r=0, then X represents O, S, $NR_{18}$, $CR_{20}$,
if r=1, then X represents $CR_{20}$,
$R_{15}$ and $R_{18}$ have the same definition as $R_1$ defined above,
$R_{16}$, $R_{17}$, $R_{19}$, $R_{20}$ and $R_{21}$ have the same definition as $R_2$ defined above,
V'' represents an organic or inorganic anion, with the condition that in formula (I), one of the groups $A_1$, $Z_2$ and $A_3$ is a cationic group.

According to the invention, when it is indicated for the groups $R_1$, $R_3$, $R_5$, $R_2$, $R_4$, $R_6$, $R_8$, $R'_8$, $R_7$, $R'7$, $R_9$, $R'_9$, B, $R_{10}$, $R_{11}$, $R_{12}$, $R_{13}$, $R_{14}$, $Z_2$ that one or more of the carbon atoms can be replaced by an oxygen, nitrogen, halogen or sulfur atom or by an $SO_2$ group, and/or that these groups are unsaturated, this means that it is possible, by way of example, to carry out the following conversions:

| | can become | |
|---|---|---|
| 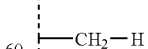 | |  |
| 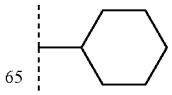 | can become | 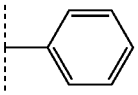 |

-continued

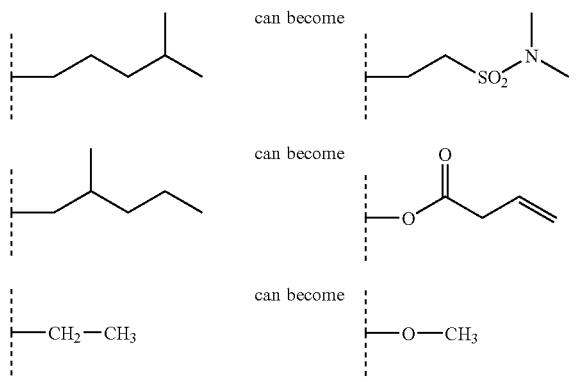

According to the present invention, the radicals $R_1$, $R_3$ and $R_5$ are preferably chosen from a $C_1$–$C_4$ alkyl or alkenyl radical which can be substituted by one or more hydroxyl, optionally substituted amino, carboxyl or sulfonic substituents; it being possible for a phenyl radical to be substituted by one or more halogen atoms, one or more $C_1$–$C_4$ alkyl, $C_1$–$C_4$ alkoxy, amino, hydroxyl, trifluoromethyl, $C_1$–$C_4$ alkylamino, carboxyl or sulfonyl groups; it being possible for a benzyl radical to be substituted by one or more halogen atoms, one or more $C_1$–$C_4$ alkyl, $C_1$–$C_4$ alkoxy, amino or trifluoromethyl groups; a heterocycle chosen from imidazole, thiazole, pyridine or pyrimidine; a radical $(CH2)_p$-T-$(CH2)_q$-$V_1R'$ where p and q are integers, which are identical or different, between 1 and 3, R' represents H or methyl and T and $V_1$ independently denote an oxygen atom or a radical NR" with R" denoting a hydrogen or a methyl.

According to the present invention defined above, preference is given for $R_1$, $R_3$ and $R_5$, more particularly to the methyl, ethyl, hydroxyethyl, aminoethyl, carboxymethyl, carboxyethyl, phenyl or benzyl radicals; the heterocycles chosen from pyridyl, imidazolyl and pyrimidinyl.

More particularly, the radicals $R_1$ and $R_3$ are chosen from the methyl, ethyl, phenyl, hydroxyethyl, aminoethyl, carboxymethyl and carboxyethyl groups.

The radicals $R_2$, $R_4$ and $R_6$ are preferably chosen from a hydrogen atom; an alkyl, for example methyl or ethyl, radical; an alkyl radical substituted by one or more hydroxyl or amino groups or a halogen, such as hydroxymethyl, hydroxyethyl, 1,2-dihydroxyethyl, 1,2-dihydroxypropyl, 2,3-dihydroxypropyl, aminomethyl, aminoethyl, aminopropyl; trifluoromethyl; it being possible for a phenyl radical to be substituted by one or more substituents chosen from the alkyl, hydroxyl, amino, alkoxy, carboxyl, trifluoromethyl and sulfonic radicals; benzyl radicals and benzyl substituted by an alkoxy, for example methoxy or hydroxy, in particular 2-methoxybenzyl, 3-methoxybenzyl, 4-methoxybenzyl, 2-hydroxybenzyl, 3-hydroxybenzyl, 4-hydroxybenzyl; a heterocycle chosen from N-pyrrolidinyl, N-piperidinyl, N-morpholine, N-piperazinyl or N-imidazolyl; an alkoxy, such as methoxy or ethoxy, radical; a phosphonyl radical; a siloxy radical; an amino radical; a $C_1$–$C_4$ (di)alkylamino radical; an acyl radical; an acylamino radical; a sulfonamide radical; a ureido radical; a sulfonylamino radical.

The preferred radicals $R_2$, $R_4$ and $R_6$ are hydrogen; an alkyl radical chosen from methyl, ethyl; a substituted alkyl radical chosen from trifluoromethyl; hydroxymethyl, hydroxyethyl, aminomethyl, aminoethyl; a benzyl; a phenyl optionally substituted by one or more radicals chosen from the methyl, hydroxyl, amino and methoxy radicals; 2-methoxybenzyl; 4-methoxybenzyl; 2-hydroxybenzyl; 4-hydroxybenzyl; a heterocycle chosen from pyrrolidinyl, piperidinyl; a methoxy radical; an acyl radical; an amino radical; a $C_1$–$C_4$ (di)alkylamino radical. More particularly, the radicals $R_2$, $R_4$ and $R_6$ are chosen from hydrogen; methyl; ethyl; trifluoromethyl; phenyl; pyrrolidinyl; methoxy; amino.

$R_8$ and $R'_8$ are preferably chosen from a $C_1$–$C_4$ alkyl or alkenyl radical which can be substituted by one or more hydroxyl, optionally substituted amino or carboxyl substituents; it being possible for a phenyl radical to be substituted by one or more halogen atoms, one or more $C_1$–$C_4$ alkyl, $C_1$–$C_4$ alkoxy, amino, hydroxyl, trifluoromethyl, $C_1$–$C_4$ alkylamino, carboxyl or sulfonyl groups; a heterocycle chosen from imidazole, thiazole, pyridine or pyrimidine; a radical $(CH2)_p$-T-$(CH2)_q$-$V_1R'$ where p and q are integers, which are identical or different, between 1 and 3, R' represents H or methyl and T and $V_1$ independently denote an oxygen atom or a radical NR" with R" denoting a hydrogen or a methyl.

According to the present invention defined above, preference is given, for $R_8$ and $R'_8$, more particularly to the hydrogen, methyl, ethyl, hydroxyethyl, aminoethyl, carboxymethyl, carboxyethyl and phenyl radicals; the heterocycles chosen from pyridynyl, imidazolyl and pyrimidinyl. More particularly, the radicals $R_8$ and $R'_8$ are chosen from the hydrogen, methyl, ethyl, phenyl, hydroxyethyl, aminoethyl, carboxymethyl and carboxyethyl groups.

B is preferably chosen from an optionally substituted alkyl radical chosen from methyl, ethyl, propyl; hydroxymethyl, hydroxyethyl, aminomethyl, aminoethyl; a methoxybenzyl; a heterocycle chosen from piperazinyl. More particularly, the radical B is chosen from methyl; ethyl; propyl; phenyl; piperazinyl; triazine.

$R_{10}$, $R_{11}$, $R_{12}$, $R_{13}$ and $R_{14}$ are preferably chosen from a hydrogen; a $C_1$–$C_4$ alkyl or alkenyl radical which can be substituted by a hydroxyl or an optionally substituted amino substituent; a phenyl radical which can be substituted by one or more halogen atoms, one or more $C_1$–$C_4$ alkyl, $C_1$–$C_4$ alkoxy, amino, hydroxyl, trifluoromethyl, $C_1$–$C_4$ alkylamino, carboxyl or sulfonyl groups; a benzyl radical which can be substituted by one or more halogen atoms, one or more $C_1$–$C_4$ alkyl, $C_1$–$C_4$ alkoxy, amino or trifluoromethyl groups; a $C_1$–$C_4$ (poly)aminoalkyl radical; a radical $(CH2)_p$-T-$(CH2)_q$-VR' where p and q are integers, which are identical or different, between 1 and 3, R' represents H or methyl and T and V independently denote an oxygen atom or a radical NR" with R" denoting a hydrogen or a methyl, a sulfonyl radical.

According to the present invention defined above, preference is given, for $R_{10}$, $R_{11}$, $R_{12}$, $R_{13}$ and $R_{14}$, more particularly to the methyl, ethyl, isopropyl, hydroxyethyl, aminoethyl, phenyl and benzyl radicals; the heterocycles chosen from pyridynyl, imidazolyl and pyrimidinyl. More particularly, the radicals $R_{10}$, $R_{11}$, $R_{12}$, $R_{13}$ and $R_{14}$ are chosen from the methyl, ethyl, phenyl, hydroxyethyl, aminoethyl, carboxymethyl and carboxyethyl groups.

Z1 is preferably chosen from the group consisting of imidazolinium, triazolinium, thiazolinium, pyridinium and pyridazinium radicals optionally substituted on the carbon atoms of the ring by a methyl, a methoxy, a carboxyl, an amino, a phenyl, a pyrrolidine, and on the nitrogen atom by a methyl, a 2-hydroxyethyl, a carboxymethyl or a carboxyethyl.

$Z_2$ is preferably chosen from the imidazolium, pyridinium, pyridazinium, pyrimidinium and pyrazinium radicals.

$A_2$ is preferably chosen from the pyrazolyl, pyrrolyl, imidazolyl, triazolyl and thiadiazolyl radicals which are optionally substituted.

$A_1$, $A_3$ represent, independently of one another, an aniline, aminopyridinyl or aminopyridazinyl radical optionally substituted by a hydrogen atom, by an alkyl radical, for example chosen from methyl, ethyl, a substituted alkyl, for example hydroxymethyl, hydroxyethyl, 1,2-dihydroxyethyl, 1,2-dihydroxypropyl, 2,3-dihydroxypropyl, aminomethyl, aminoethyl, aminopropyl; by a trifluoromethyl radical; by a heterocycle chosen from N-pyrrolidinyl, N-piperidinyl, N-morpholine, N-piperazinyl or N-imidazolyl, by an alkoxy, such as methoxy or ethoxy, radical, by a phosphonyl radical, by a siloxy radical, by a 1,2-diaminoethyl radical, by a 2,3-diaminopropyl radical, by an acyl radical, by an acylamino radical, by a sulfonamide radical, by a ureido radical, by a sulfonylamino radical.

The preferred pairs ($A_1$, $A_3$) are chosen from (aniline radical, aniline radical), (aniline radical, aminopyridinyl radical), (aminopyridinyl radical, aniline radical). Independently, each of the radicals constituting these pairs is optionally substituted by a hydrogen atom, or by an alkyl radical chosen from methyl and ethyl, or by an optionally substituted alkyl radical chosen from hydroxymethyl, 1,2-dihydroxyethyl, aminomethyl, 2-aminoethyl, 1,2-diaminoethyl, 2,3-diaminopropyl or by a heterocycle chosen from pyrrolidinyl, piperidinyl, or by a methoxy, amino, methylamino, dimethylamino or 2-hydroxyethylamino radical.

The following pairs ($A_1$, $A_3$) will be more particularly chosen: (aniline radical, aniline radical) optionally substituted by a methyl or ethyl radical, or by a hydroxymethyl, 1,2-dihydroxyethyl, aminomethyl, 2-aminoethyl, 1,2-diaminoethyl or 2,3-diaminopropyl radical or by a pyrrolidinyl or piperidinyl radical, or by a methoxy, amino, methylamino, dimethylamino or 2-hydroxyethylamino radical.

In the context of the invention, the organic or inorganic anion of formulae (I) or (II) can be chosen from a halide such as chloride, bromide, fluoride, iodide; a hydroxide; a sulfate; a hydrogen sulfate; a ($C_1$–$C_6$)alkyl sulfate such as for example a methyl sulfate or an ethyl sulfate; an acetate; a tatrate; an oxalate; a ($C_1$–$C_6$)alkyl sulfonate such as methyl sulfonate; an aryl sulfonate which is unsubstituted or substituted by a $C_1$–$C_4$ alkyl radical such as for example a 4-toluoyl sulfonate.

In the context of the invention, the azo dyes of formula (I) are preferably chosen from the following dyes:

| Compound | $Z_1$ | $A_1$ | $A_3$ | n | $Z_2$ |
|---|---|---|---|---|---|
| 1 | 2-imidazolinium | (p-phenylene-NH) | | 0 | 2-imidazolinium |
| 2 | 2-imidazolinium | (p-phenylene-NH) | (p-phenylene-NH) | 1 | 2-imidazolinium |
| 3 | 2-imidazolinium | (pyridine-2-yl-NH) | | 0 | 2-imidazolinium |
| 4 | 2-imidazolinium | (p-phenylene-NH) | (pyridine-2-yl-NH) | 1 | 2-imidazolinium |
| 5 | 2-imidazolinium | (2-methoxy-p-phenylene-NH) | | 0 | 2-imidazolinium |
| 6 | 2-imidazolinium | (2-methoxy-p-phenylene-NH) | (p-phenylene-NH) | 1 | 2-imidazolinium |

-continued

| Compound | Z₁ | A₁ | A₃ | n | Z₂ |
|---|---|---|---|---|---|
| 7 | 2-imidazolinium | [3-OMe-pyridin-2-yl-NH- attached at 5-position] | | 0 | 2-imidazolinium |
| 8 | 2-imidazolinium | [2-OMe-phenyl-NH- attached at 4-position] | [pyridin-2-yl-NH- attached at 5-position] | 1 | 2-imidazolinium |
| 9 | 2-imidazolinium | [2,5-diOMe-phenyl-NH-] | | 0 | 2-imidazolinium |
| 10 | 2-imidazolinium | [2,5-diOMe-phenyl-NH-] | [phenyl-NH-] | 1 | 2-imidazolinium |
| 11 | 2-imidazolinium | [3,6-diOMe-pyridin-2-yl-NH-] | | 0 | 2-imidazolinium |
| 12 | 2-imidazolinium | [2,5-diOMe-phenyl-NH-] | [pyridin-2-yl-NH-] | 1 | 2-imidazolinium |
| 13 | 2-imidazolinium | [3-Me-phenyl-NH-] | | 0 | 2-imidazolinium |
| 14 | 2-imidazolinium | [3-Me-phenyl-NH-] | [phenyl-NH-] | 1 | 2-imidazolinium |
| 15 | 2-imidazolinium | [4-Me-pyridin-2-yl-NH-] | | 0 | 2-imidazolinium |

-continued

| Compound | $Z_1$ | $A_1$ | $A_3$ | n | $Z_2$ |
|---|---|---|---|---|---|
| 16 | 2-imidazolinium | 3-methyl-4-aminophenyl (NH-linked) | 6-amino-pyridin-3-yl (NH-linked) | 1 | 2-imidazolinium |
| 17 | 2-triazolinium | 4-aminophenyl (NH-linked) | — | 0 | 2-imidazolinium |
| 18 | 2-triazolinium | 4-aminophenyl (NH-linked) | 4-aminophenyl (NH-linked) | 1 | 2-imidazolinium |
| 19 | 2-triazolinium | 6-amino-pyridin-3-yl (NH-linked) | — | 0 | 2-imidazolinium |
| 20 | 2-triazolinium | 4-aminophenyl (NH-linked) | 6-amino-pyridin-3-yl (NH-linked) | 1 | 2-imidazolinium |
| 21 | 2-triazolinium | 2-methoxy-4-aminophenyl (NH-linked) | — | 0 | 2-imidazolinium |
| 22 | 2-triazolinium | 2-methoxy-4-aminophenyl (NH-linked) | 4-aminophenyl (NH-linked) | 1 | 2-imidazolinium |
| 23 | 2-triazolinium | 3-methoxy-2-amino-pyridin-5-yl (NH-linked) | — | 0 | 2-imidazolinium |
| 24 | 2-triazolinium | 2-methoxy-4-aminophenyl (NH-linked) | 6-amino-pyridin-3-yl (NH-linked) | 1 | 2-imidazolinium |
| 25 | 2-triazolinium | 2,5-dimethoxy-4-aminophenyl (NH-linked) | — | 0 | 2-imidazolinium |

-continued

| Compound | $Z_1$ | $A_1$ | $A_3$ | n | $Z_2$ |
|---|---|---|---|---|---|
| 26 | 2-triazolinium | 2,5-dimethoxy-phenyl-NH- | 1,4-phenyl-NH- | 1 | 2-imidazolinium |
| 27 | 2-triazolinium | 3,6-dimethoxy-pyridin-2-yl-NH- | | 0 | 2-imidazolinium |
| 28 | 2-triazolinium | 2,5-dimethoxy-phenyl-NH- | 6-(pyridin-2-yl)-NH- | 1 | 2-imidazolinium |
| 29 | 2-triazolinium | 2-methyl-phenyl-NH- | | 0 | 2-imidazolinium |
| 30 | 2-triazolinium | 2-methyl-phenyl-NH- | 1,4-phenyl-NH- | 1 | 2-imidazolinium |
| 31 | 2-triazolinium | 4-methyl-pyridin-2-yl-NH- | | 0 | 2-imidazolinium |
| 32 | 2-triazolinium | 2-methyl-phenyl-NH- | 6-(pyridin-2-yl)-NH- | 1 | 2-imidazolinium |
| 33 | 3-pyridinium | 1,4-phenyl-NH- | | 0 | 2-imidazolinium |
| 34 | 3-pyridinium | 6-(pyridin-2-yl)-NH- | 1,4-phenyl-NH- | 1 | 2-imidazolinium |
| 35 | 3-pyridinium | 6-(pyridin-2-yl)-NH- | | 0 | 2-imidazolinium |

-continued

| Compound | $Z_1$ | $A_1$ | $A_3$ | n | $Z_2$ |
|---|---|---|---|---|---|
| 36 | 3-pyridinium | phenyl-NH- | 5-(2-aminopyridinyl)- | 1 | 2-imidazolinium |
| 37 | 3-pyridinium | 3-OMe-phenyl-NH- | — | 0 | 2-imidazolinium |
| 38 | 3-pyridinium | 2-OMe-phenyl-NH- | phenyl-NH- | 1 | 2-imidazolinium |
| 39 | 3-pyridinium | 3-OMe-pyridinyl-NH- | — | 0 | 2-imidazolinium |
| 40 | 3-pyridinium | 2-OMe-phenyl-NH- | 5-(2-aminopyridinyl)- | 1 | 2-imidazolinium |
| 41 | 3-pyridinium | 2,5-di-OMe-phenyl-NH- | — | 0 | 2-imidazolinium |
| 42 | 3-pyridinium | 2,5-di-OMe-phenyl-NH- | phenyl-NH- | 1 | 2-imidazolinium |
| 43 | 3-pyridinium | 3,6-di-OMe-pyridinyl-NH- | — | 0 | 2-imidazolinium |
| 44 | 3-pyridinium | 2,5-di-OMe-phenyl-NH- | 5-(2-aminopyridinyl)- | 1 | 2-imidazolinium |

-continued

| Compound | $Z_1$ | $A_1$ | $A_3$ | n | $Z_2$ |
|---|---|---|---|---|---|
| 45 | 3-pyridinium | methyl-substituted aminophenyl | | 0 | 2-imidazolinium |
| 46 | 3-pyridinium | methyl-substituted aminophenyl | aminophenyl | 1 | 2-imidazolinium |
| 47 | 3-pyridinium | methyl-substituted aminopyridyl | | 0 | 2-imidazolinium |
| 48 | 3-pyridinium | methyl-substituted aminophenyl | aminopyridyl | 1 | 2-imidazolinium |
| 49 | 2-imidazolinium | methyl-substituted aminophenyl | | 0 | 2-pyridinium |
| 50 | 2-imidazolinium | OMe-substituted aminophenyl | | 0 | 2-pyridinium |
| 51 | 2-imidazolinium | aminopyridyl | | 0 | 2-pyridinium |
| 52 | 2-imidazolinium | OMe-substituted aminopyridyl | | 0 | 2-pyridinium |
| 53 | 2-imidazolinium | OMe-substituted aminophenyl | aminophenyl | 1 | 2-pyridinium |
| 54 | 2-imidazolinium | di-OMe-substituted aminophenyl | | 0 | 2-pyridinium |

-continued

| Compound | $Z_1$ | $A_1$ | $A_3$ | n | $Z_2$ |
|---|---|---|---|---|---|
| 55 | 2-imidazolinium | 2-methoxy-4-substituted anilinyl | 5-substituted-2-aminopyridinyl | 1 | 2-pyridinium |
| 56 | 2-imidazolinium | 3,6-dimethoxy-5-substituted-2-aminopyridinyl | | 0 | 2-pyridinium |
| 57 | 2-imidazolinium | 2,5-dimethoxy-4-substituted anilinyl | 4-substituted anilinyl | 1 | 2-pyridinium |
| 58 | 2-imidazolinium | 3-methyl-4-substituted anilinyl | | 0 | 2-pyridinium |
| 59 | 2-imidazolinium | 3-methyl-4-substituted anilinyl | 4-substituted anilinyl | 1 | 2-pyridinium |
| 60 | 2-imidazolinium | 4-methyl-5-substituted-2-aminopyridinyl | | 0 | 2-pyridinium |
| 61 | 2-imidazolinium | 3-methyl-4-substituted anilinyl | 5-substituted-2-aminopyridinyl | 1 | 2-pyridinium |
| 62 | 2-triazolinium | 4-substituted anilinyl | | 0 | 2-pyridinium |
| 63 | 2-triazolinium | 5-substituted-2-aminopyridinyl | 4-substituted anilinyl | 1 | 2-pyridinium |
| 64 | 2-triazolinium | 5-substituted-2-aminopyridinyl | | 0 | 2-pyridinium |

-continued

| Compound | $Z_1$ | $A_1$ | $A_3$ | n | $Z_2$ |
|---|---|---|---|---|---|
| 65 | 2-triazolinium | phenyl-NH- | pyridin-2-yl-NH- (5-linked) | 1 | 2-pyridinium |
| 66 | 2-triazolinium | 2-OMe-phenyl-NH- | — | 0 | 2-pyridinium |
| 67 | 2-triazolinium | 2-OMe-phenyl-NH- | phenyl-NH- | 1 | 2-pyridinium |
| 68 | 2-triazolinium | 3-OMe-pyridin-2-yl-NH- | — | 0 | 2-pyridinium |
| 69 | 2-triazolinium | 2-OMe-phenyl-NH- | pyridin-2-yl-NH- (5-linked) | 1 | 2-pyridinium |
| 70 | 2-triazolinium | 2,5-di-OMe-phenyl-NH- | — | 0 | 2-pyridinium |
| 71 | 2-triazolinium | 2,5-di-OMe-phenyl-NH- | phenyl-NH- | 1 | 2-pyridinium |
| 72 | 2-triazolinium | 3,6-di-OMe-pyridin-2-yl-NH- | — | 0 | 2-pyridinium |
| 73 | 2-triazolinium | 2,5-di-OMe-phenyl-NH- | pyridin-2-yl-NH- (5-linked) | 1 | 2-pyridinium |

-continued

| Compound | $Z_1$ | $A_1$ | $A_3$ | n | $Z_2$ |
|---|---|---|---|---|---|
| 74 | 2-triazolinium | 3-methyl-4-aminophenyl | | 0 | 2-pyridinium |
| 75 | 2-triazolinium | 3-methyl-4-aminophenyl | 4-aminophenyl | 1 | 2-pyridinium |
| 76 | 2-triazolinium | 4-methyl-2-aminopyridinyl | | 0 | 2-pyridinium |
| 77 | 2-triazolinium | 3-methyl-4-aminophenyl | 2-amino-5-pyridinyl | 1 | 2-pyridinium |
| 78 | 3-pyridinium | 4-aminophenyl | | 0 | 2-pyridinium |
| 79 | 3-pyridinium | 4-aminophenyl | 4-aminophenyl | 1 | 2-pyridinium |
| 80 | 3-pyridinium | 2-amino-5-pyridinyl | | 0 | 2-pyridinium |
| 81 | 3-pyridinium | 4-aminophenyl | 2-amino-5-pyridinyl | 1 | 2-pyridinium |
| 82 | 3-pyridinium | 2-methoxy-4-aminophenyl | | 0 | 2-pyridinium |
| 83 | 3-pyridinium | 2-methoxy-4-aminophenyl | 4-aminophenyl | 1 | 2-pyridinium |

-continued
| Compound | $Z_1$ | $A_1$ | $A_3$ | n | $Z_2$ |
|---|---|---|---|---|---|
| 84 | 3-pyridinium | 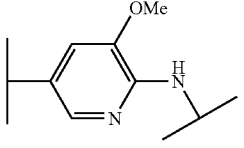 |  | 0 | 2-pyridinium |
| 85 | 3-pyridinium | 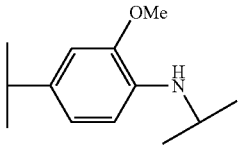 | 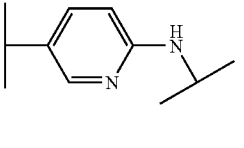 | 1 | 2-pyridinium |
| 86 | 3-pyridinium | 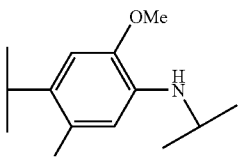 |  | 0 | 2-pyridinium |
| 87 | 3-pyridinium | 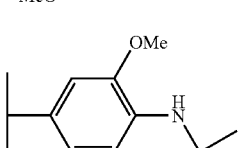 | 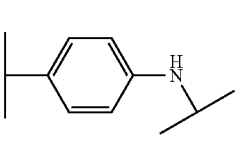 | 1 | 2-pyridinium |
| 88 | 3-pyridinium | 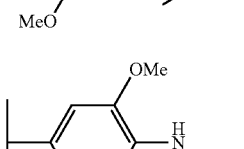 |  | 0 | 2-pyridinium |
| 89 | 3-pyridinium | 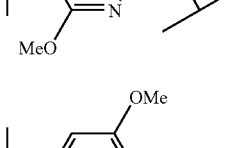 | 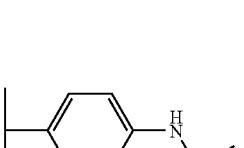 | 1 | 2-pyridinium |
| 90 | 3-pyridinium | 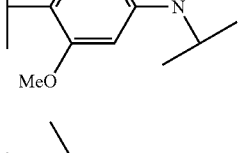 |  | 0 | 2-pyridinium |
| 91 | 3-pyridinium | 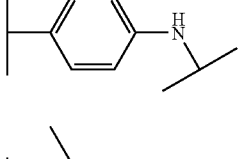 | 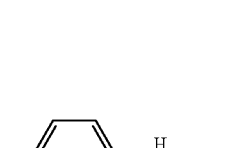 | 1 | 2-pyridinium |
| 92 | 3-pyridinium | 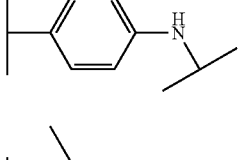 |  | 0 | 2-pyridinium |

-continued
| Compound | Z₁ | A₁ | A₃ | n | Z₂ |
|---|---|---|---|---|---|
| 93 | 3-pyridinium | 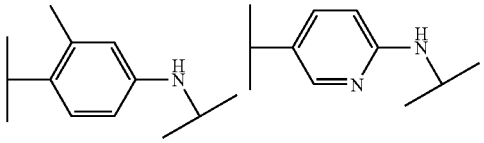 | 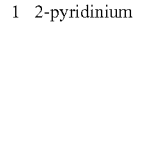 | 1 | 2-pyridinium |
| 94 | 2-imidazolinium | 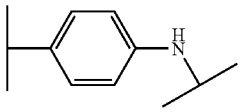 |  | 0 | 3-pyridazinium |
| 95 | 2-imidazolinium | 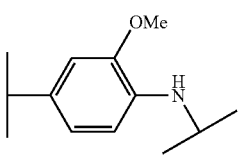 |  | 0 | 3-pyridazinium |
| 96 | 2-imidazolinium | 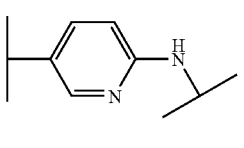 |  | 0 | 3-pyridazinium |
| 97 | 2-imidazolinium | 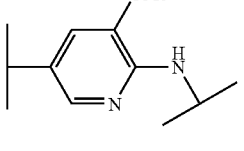 |  | 0 | 3-pyridazinium |
| 98 | 2-imidazolinium | 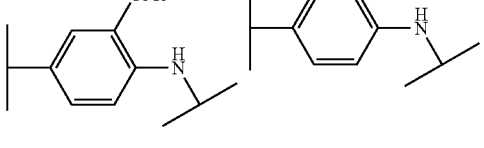 | 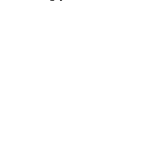 | 1 | 3-pyridazinium |
| 99 | 2-imidazolinium | 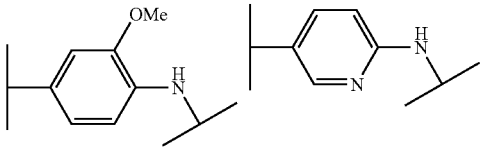 | 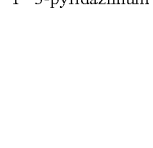 | 1 | 3-pyridazinium |
| 100 | 2-imidazolinium | 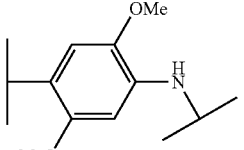 |  | 0 | 3-pyridazinium |
| 101 | 2-imidazolinium | 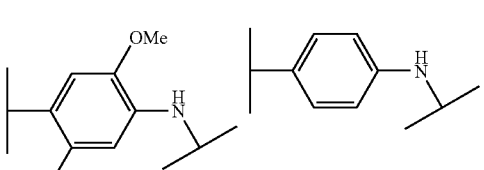 | 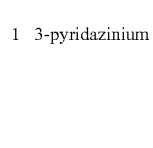 | 1 | 3-pyridazinium |

-continued

| Compound | $Z_1$ | $A_1$ | $A_3$ | n | $Z_2$ |
|---|---|---|---|---|---|
| 102 | 2-imidazolinium | 3-OMe, 6-MeO pyridine-2-ylamino (5-yl attachment) | | 0 | 3-pyridazinium |
| 103 | 2-imidazolinium | 2-OMe, 5-MeO phenylamino (4-yl) | pyridin-2-ylamino (5-yl) | 1 | 3-pyridazinium |
| 104 | 2-imidazolinium | 3-methylphenylamino (4-yl) | | 0 | 3-pyridazinium |
| 105 | 2-imidazolinium | 3-methylphenylamino (4-yl) | phenylamino (4-yl) | 1 | 3-pyridazinium |
| 106 | 2-imidazolinium | 4-methylpyridin-2-ylamino (5-yl) | | 0 | 3-pyridazinium |
| 107 | 2-imidazolinium | 3-methylphenylamino (4-yl) | pyridin-2-ylamino (5-yl) | 1 | 3-pyridazinium |
| 108 | 2-triazolinium | phenylamino (4-yl) | | 0 | 3-pyridazinium |
| 109 | 2-triazolinium | pyridin-2-ylamino (5-yl) | phenylamino (4-yl) | 1 | 3-pyridazinium |
| 110 | 2-triazolinium | pyridin-2-ylamino (5-yl) | | 0 | 3-pyridazinium |
| 111 | 2-triazolinium | phenylamino (4-yl) | pyridin-2-ylamino (5-yl) | 1 | 3-pyridazinium |

-continued

| Compound | $Z_1$ | $A_1$ | $A_3$ | n | $Z_2$ |
|---|---|---|---|---|---|
| 112 | 2-triazolinium | 2-OMe-4-aminophenyl | | 0 | 3-pyridazinium |
| 113 | 2-triazolinium | 2-OMe-4-aminophenyl | 4-aminophenyl | 1 | 3-pyridazinium |
| 114 | 2-triazolinium | 3-OMe-2-amino-5-pyridyl | | 0 | 3-pyridazinium |
| 115 | 2-triazolinium | 2-OMe-4-aminophenyl | 6-amino-3-pyridyl | 1 | 3-pyridazinium |
| 116 | 2-triazolinium | 2,5-di-OMe-4-aminophenyl | | 0 | 3-pyridazinium |
| 117 | 2-triazolinium | 2,5-di-OMe-4-aminophenyl | 4-aminophenyl | 1 | 3-pyridazinium |
| 118 | 2-triazolinium | 3,6-di-OMe-2-amino-5-pyridyl | | 0 | 3-pyridazinium |
| 119 | 2-triazolinium | 2,5-di-OMe-4-aminophenyl | 6-amino-3-pyridyl | 1 | 3-pyridazinium |
| 120 | 2-triazolinium | 3-methyl-4-aminophenyl | | 0 | 3-pyridazinium |

-continued

| Compound | $Z_1$ | $A_1$ | $A_3$ | n | $Z_2$ |
|---|---|---|---|---|---|
| 121 | 2-triazolinium | 3-methyl-4-phenylamino | 4-phenylamino | 1 | 3-pyridazinium |
| 122 | 2-triazolinium | 4-methyl-5-(2-pyridylamino) | | 0 | 3-pyridazinium |
| 123 | 2-triazolinium | 3-methyl-4-phenylamino | 5-(2-pyridylamino) | 1 | 3-pyridazinium |
| 124 | 3-pyridinium | 4-phenylamino | | 0 | 3-pyridazinium |
| 125 | 3-pyridinium | 4-phenylamino | 4-phenylamino | 1 | 3-pyridazinium |
| 126 | 3-pyridinium | 5-(2-pyridylamino) | | 0 | 3-pyridazinium |
| 127 | 3-pyridinium | 4-phenylamino | 5-(2-pyridylamino) | 1 | 3-pyridazinium |
| 128 | 3-pyridinium | 2-OMe-4-phenylamino | | 0 | 3-pyridazinium |
| 129 | 3-pyridinium | 2-OMe-4-phenylamino | 4-phenylamino | 1 | 3-pyridazinium |
| 130 | 3-pyridinium | 3-OMe-5-(2-pyridylamino) | | 0 | 3-pyridazinium |

-continued
| Compound | $Z_1$ | $A_1$ | $A_3$ | n | $Z_2$ |
|---|---|---|---|---|---|
| 131 | 3-pyridinium | 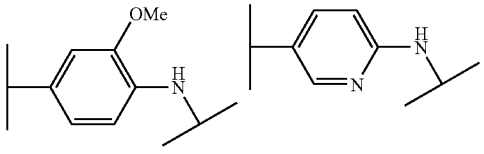 | 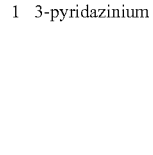 | 1 | 3-pyridazinium |
| 132 | 3-pyridinium | 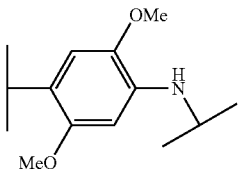 | | 0 | 3-pyridazinium |
| 133 | 3-pyridinium | 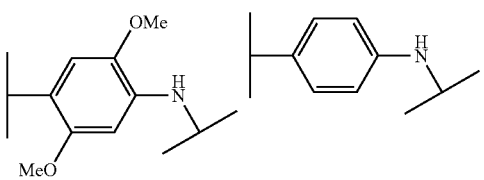 | 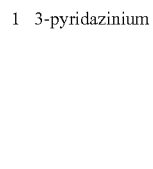 | 1 | 3-pyridazinium |
| 134 | 3-pyridinium | 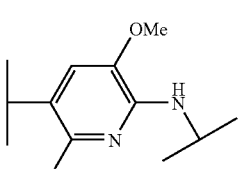 | | 0 | 3-pyridazinium |
| 135 | 3-pyridinium | 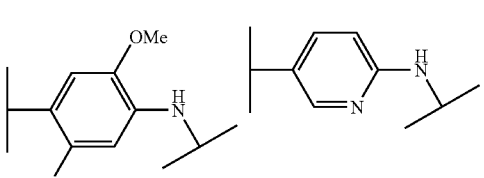 | 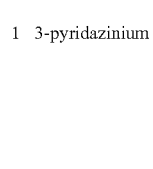 | 1 | 3-pyridazinium |
| 136 | 3-pyridinium | 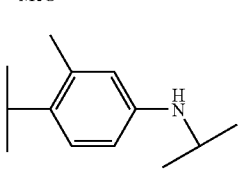 | | 0 | 3-pyridazinium |
| 137 | 3-pyridinium | 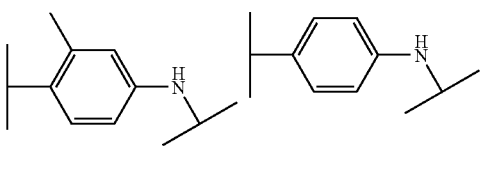 | 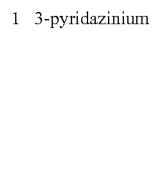 | 1 | 3-pyridazinium |
| 138 | 3-pyridinium | 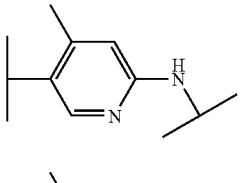 | | 0 | 3-pyridazinium |
| 139 | 3-pyridinium | 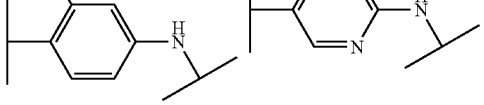 |  | 1 | 3-pyridazinium |

Preferably, the preferred compounds which may be synthesized according to the procedure described in the examples are chosen from

| Compound | $Z_1$ | $A_1$ | $A_3$ | n | $Z_2$ |
|---|---|---|---|---|---|
| 1 | 2-imidazolinium | [p-phenylene-NH] | | 0 | 2-imidazolinium |
| 2 | 2-imidazolinium | [p-phenylene-NH] | [p-phenylene-NH] | 1 | 2-imidazolinium |
| 3 | 2-imidazolinium | [pyridyl-NH] | | 0 | 2-imidazolinium |
| 4 | 2-imidazolinium | [p-phenylene-NH] | [pyridyl-NH] | 1 | 2-imidazolinium |
| 5 | 2-imidazolinium | [OMe-phenylene-NH] | | 0 | 2-imidazolinium |
| 6 | 2-imidazolinium | [OMe-phenylene-NH] | [p-phenylene-NH] | 1 | 2-imidazolinium |
| 7 | 2-imidazolinium | [OMe-pyridyl-NH] | | 0 | 2-imidazolinium |
| 8 | 2-imidazolinium | [OMe-phenylene-NH] | [pyridyl-NH] | 1 | 2-imidazolinium |
| 9 | 2-imidazolinium | [di-OMe-phenylene-NH] | | 0 | 2-imidazolinium |
| 18 | 2-triazolinium | [p-phenylene-NH] | [p-phenylene-NH] | 1 | 2-imidazolinium |

-continued

| Compound | $Z_1$ | $A_1$ | $A_3$ | n | $Z_2$ |
|---|---|---|---|---|---|
| 25 | 2-triazolinium | 2,5-dimethoxy-phenyl-NH | | 0 | 2-imidazolinium |
| 26 | 2-triazolinium | 2,5-dimethoxy-phenyl-NH | phenyl-NH | 1 | 2-imidazolinium |
| 29 | 2-triazolinium | 2-methyl-phenyl-NH | | 0 | 2-imidazolinium |
| 30 | 2-triazolinium | 2-methyl-phenyl-NH | phenyl-NH | 1 | 2-imidazolinium |
| 34 | 3-pyridinium | phenyl-NH | phenyl-NH | 1 | 2-imidazolinium |
| 41 | 3-pyridinium | 2,5-dimethoxy-phenyl-NH | | 0 | 2-imidazolinium |
| 45 | 3-pyridinium | 2-methyl-phenyl-NH | | 0 | 2-imidazolinium |
| 49 | 2-imidazolinium | phenyl-NH | | 0 | 2-pyridinium |
| 50 | 2-imidazolinium | phenyl-NH | phenyl-NH | 1 | 2-pyridinium |
| 51 | 2-imidazolinium | pyridyl-NH | | 0 | 2-pyridinium |

-continued

| Compound | $Z_1$ | $A_1$ | $A_3$ | n | $Z_2$ |
|---|---|---|---|---|---|
| 54 | 2-imidazolinium | 2,5-di(OMe)-phenyl-NH- | | 0 | 2-pyridinium |
| 61 | 2-imidazolinium | methyl-phenyl-NH- | pyridinyl-NH- | 1 | 2-pyridinium |
| 78 | 3-pyridinium | phenyl-NH- | | 0 | 2-pyridinium |
| 79 | 3-pyridinium | phenyl-NH- | phenyl-NH- | 1 | 2-pyridinium |
| 86 | 3-pyridinium | 2,5-di(OMe)-phenyl-NH- | | 0 | 2-pyridinium |
| 87 | 3-pyridinium | 2,5-di(OMe)-phenyl-NH- | phenyl-NH- | 1 | 2-pyridinium |
| 94 | 2-imidazolinium | phenyl-NH- | | 0 | 3-pyridazinium |
| 95 | 2-imidazolinium | phenyl-NH- | phenyl-NH- | 1 | 3-pyridazinium |
| 100 | 2-imidazolinium | 2,5-di(OMe)-phenyl-NH- | | 0 | 3-pyridazinium |
| 101 | 2-imidazolinium | 2,5-di(OMe)-phenyl-NH- | phenyl-NH- | 1 | 3-pyridazinium |

-continued

| Compound | $Z_1$ | $A_1$ | $A_3$ | n | $Z_2$ |
|---|---|---|---|---|---|
| 105 | 2-imidazolinium | 3-methyl-4-(NH)phenyl | 4-(NH)phenyl | 1 | 3-pyridazinium |
| 109 | 2-triazolinium | 4-(NH)phenyl | 4-(NH)phenyl | 1 | 3-pyridazinium |
| 116 | 2-triazolinium | 2,5-dimethoxy-4-(NH)phenyl | — | 0 | 3-pyridazinium |
| 121 | 2-triazolinium | 3-methyl-4-(NH)phenyl | 4-(NH)phenyl | 1 | 3-pyridazinium |
| 124 | 3-pyridinium | 4-(NH)phenyl | — | 0 | 3-pyridazinium |
| 125 | 3-pyridinium | 4-(NH)phenyl | 4-(NH)phenyl | 1 | 3-pyridazinium |
| 130 | 3-pyridinium | 3-OMe-2-(NH)pyridyl | — | 0 | 3-pyridazinium |
| 131 | 3-pyridinium | 2-OMe-4-(NH)phenyl | 2-(NH)-5-pyridyl | 1 | 3-pyridazinium |
| 132 | 3-pyridinium | 2,5-dimethoxy-4-(NH)phenyl | — | 0 | 3-pyridazinium |
| 133 | 3-pyridinium | 2,5-dimethoxy-4-(NH)phenyl | 4-(NH)phenyl | 1 | 3-pyridazinium |

| Compound | $Z_1$ | $A_1$ | $A_3$ | n | $Z_2$ |
|---|---|---|---|---|---|
| 136 | 3-pyridinium | 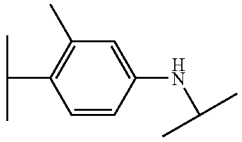 | | 0 | 3-pyridazinium |
| 137 | 3-pyridinium | 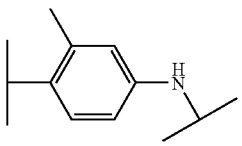 | 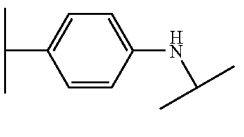 | 1 | 3-pyridazinium |

The concentration of cationic azo dye of formula (I) can vary between 0.001 and 5% by weight approximately relative to the total weight of the dyeing composition, and preferably between approximately 0.05 and 2%.

The composition of the invention can furthermore comprise an oxidizing agent. This oxidizing agent can be any oxidizing agent conventionally used for bleaching keratinous fibers. The oxidizing agent is preferably chosen from hydrogen peroxide, urea peroxide, alkali metal bromates, persalts such as perborates and persulfates. The use of hydrogen peroxide is particularly preferred.

The composition according to the invention can furthermore comprise an oxidation base. This oxidation base can be chosen from the oxidation bases conventionally used in oxidation dyeing, for example para-phenylenediamines, bisphenylalkylenediamines, para-aminophenols, ortho-aminophenols and heterocyclic bases.

Mention may more particularly be made, among para-phenylenediamines, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-(aminophenyl)pyrrolidine, 2-thienyl-para-phenylenediamine, 2-(β-hydroxyethylamino)-5-aminotoluene, and their addition salts with an acid.

Among the para-phenylenediamines mentioned above, para-phenylenediamine, para-tolylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, and their addition salts with an acid, are particularly preferred.

Mention may be made, among bisphenylalkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)-ethylenediamine, 1,8-bis(2,5-diaminophenoxy)-3,6-dioxaoctane, and their addition salts with an acid.

Mention may be made, among para-aminophenols, by way of example, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-(2-aminomethyl)phenol, 4-amino-2-[(β-hydroxy-ethyl)aminomethyl]phenol, 4-amino-2-fluorophenol, and their addition salts with an acid.

Mention may be made, among ortho-aminophenols, by way of example, of 2-aminophenol, 2-amino-5-methylphenol, 2-amino-6-methylphenol, 5-acetamido-2-aminophenol, and their addition salts with an acid.

Mention may be made, among heterocyclic bases, by way of example, of pyridine derivatives, pyrimidine derivatives and pyrazole derivatives.

Mention may be made, among pyridine derivatives, of the compounds disclosed, for example, in Patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Mention may be made, among pyrimidine derivatives, of the compounds disclosed, for example, in Patents DE 2 359 399, JP 88-169 571, JP 05 163 124 or EP 0 770 375 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine or 2,5,6-triaminopyrimidine, and pyrazolopyrimidine derivatives, such as those mentioned in Patent Application FR-A-2 750 048, among which may be mentioned pyrazolo[1,5-a]pyrimidine-3,7-diamine, 2,5-dimethylpyrazolo[1,5-a]pyrimidine-3,7-diamine, pyrazolo

[1,5-a]pyrimidine-3,5-diamine, 2,7-dimethylpyrazolo[1,5-a] pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl) amino]ethanol, 2-[(7-aminopyrazolo[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a] pyrimidine-3,7-diamine, 2,5,N7,N7-tetramethylpyrazolo[1, 5-a]pyrimidine-3,7-diamine, 3-amino-5-methyl-7-(imidazolylpropylamino)pyrazolo[1,5-a]pyrimidine, and their addition salts with an acid and their tautomeric forms, when a tautomeric equilibrium exists.

Mention may be made, among pyrazole derivatives, of the compounds disclosed in Patents DE 3 843 892 and DE 4 133 957 and Patent Applications WO 94/08969, WO 94/08970, FR-A-2 733 749 and DE 195 43 988, such as 4,5-diamino-1-methylpyrazole, 4,5-diamino-1-(β-hydroxyethyl) pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl) amino-1-methylpyrazole, and their addition salts with an acid.

The composition according to the invention can additionally comprise one or more couplers conventionally used for the conventional oxidation dyeing of keratinous fibers. Mention may in particular be made, among these couplers, of meta-phenylenediamines, meta-aminophenols, meta-diphenols, naphthalene couplers and heterocyclic couplers.

Mention may be made, by way of example, of 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-(β-hydroxyethylamino)-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino) toluene, and their addition salts with an acid.

In the composition of the present invention, the coupler or couplers are generally present in an amount of between 0.001 and 10% by weight approximately of the total weight of the dyeing composition and more preferably from 0.005 to 6%. The oxidation base or bases are present in an amount preferably of between 0.001 and 10% by weight approximately of the total weight of the dyeing composition and more preferably from 0.005 to 6%.

Generally, the addition salts with an acid which can be used in the context of the dyeing compositions of the invention for the oxidation bases and the couplers are chosen in particular from hydrochlorides, hydrobromides, sulfates, citrates, succinates, tartrates, lactates, tosylates, benzenesulfonates, phosphates and acetates.

The dyeing composition in accordance with the invention can additionally contain direct dyes different from those of formula (I), it being possible for these dyes in particular to be chosen from nitro dyes of the benzene series, cationic direct dyes, direct azo dyes and direct methine dyes.

The medium acceptable for dyeing, also referred to as dyeing support, is generally composed of water or of a mixture of water and of at least one organic solvent, in order to dissolve the compounds which would not be sufficiently soluble in water. Mention may be made, as organic solvent, for example, of lower $C_1$–$C_4$ alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether; and aromatic alcohols, such as benzyl alcohol or phenoxyethanol; and their mixtures.

The solvents can be present in proportions preferably of between 1 and 40% by weight approximately with respect to the total weight of the dyeing composition and more preferably still between 5 and 30% by weight approximately.

The dyeing composition in accordance with the invention can also include various adjuvants conventionally used in hair dyeing compositions, such as anionic, cationic, nonionic, amphoteric or zwitterionic surface-active agents or their mixtures, anionic, cationic, nonionic, amphoteric or zwitterionic polymers or their mixtures, inorganic or organic thickening agents and in particular anionic, cationic, nonionic and amphoteric associative polymer thickeners, antioxidants, penetration agents, sequestering agents, fragrances, buffers, dispersing agents, conditioning agents, such as, for example, volatile or nonvolatile and modified or unmodified silicones, film-forming agents, ceramides, preservatives or opacifying agents.

These above adjuvants are generally present in an amount of, for each of them, between 0.01 and 20% by weight with respect to the weight of the composition.

Of course, a person skilled in the art will take care to choose this or these optional additional compounds so that the advantageous properties intrinsically attached to the dyeing composition in accordance with the invention are not, or not substantially, detrimentally affected by the envisaged addition or additions.

The pH of the dyeing composition in accordance with the invention is generally between 3 and 12 approximately and preferably between 5 and 11 approximately. It can be adjusted to the desired value by means of acidifying or basifying agents commonly used in dyeing keratinous fibers or alternatively using conventional buffer systems.

Mention may be made, among acidifying agents, by way of example, of inorganic or organic acids, such as hydrochloric acid, orthophosphoric acid, sulfuric acid, carboxylic acids, such as acetic acid, tartaric acid, citric acid or lactic acid, or sulfonic acids.

Mention may be made, among basifying agents, by way of example, of ammonia, alkaline carbonates, alkanolamines, such as mono-, di- and triethanolamines, and their derivatives, sodium hydroxide, potassium hydroxide and the compounds of following formula (III):

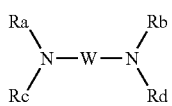

(III)

in which W is a propylene residue optionally substituted by a hydroxyl group or a $C_1$–$C_4$ alkyl radical and $R_a$, $R_b$, $R_c$ and $R_d$, which are identical or different, represent a hydrogen atom or a $C_1$–$C_4$ alkyl or $C_1$–$C_4$ hydroxyalkyl radical.

The dyeing composition according to the invention can be provided in various forms, such as in the form of liquids, creams or gels or in any other form appropriate for carrying out dyeing of keratinous fibers and in particular of human hair.

Another subject matter of the invention is a direct dyeing process which comprises the application of a dyeing composition comprising a dye of formula (I) as defined above to keratinous fibers. After a leave-in time, the keratinous fibers are rinsed, allowing colored fibers to appear.

The application to the fibers of the dyeing composition comprising the cationic azo dye of formula (I) or (II) can be carried out in the presence of an oxidizing agent which brings about the bleaching of the fiber. This oxidizing agent can be added to the composition comprising the cationic azo dye at the time of use or directly to the keratinous fiber. According to a specific embodiment, the composition comprising the cationic azo dye of formula (I) is free of oxidation base and of coupler.

Another subject matter of the invention is an oxidation dyeing process which comprises the application to fibers of a dyeing composition which comprises a dye of formula (I), at least one oxidation base and optionally at least one coupler, in the presence of an oxidizing agent.

The oxidation base, the coupler and the oxidizing agent are as defined above.

In the context of permanent oxidation dyeing, it is also possible to use, as oxidizing agent, enzymes among which may be mentioned peroxidases, 2-electron oxidoreductases, such as uricases, and 4-electron oxygenases, such as laccases.

The color can be developed at acidic, neutral or alkaline pH and the oxidizing agent can be added to the composition of the invention either at the time of use or it can be employed from an oxidizing composition comprising it, applied to the fibers simultaneously with or sequentially to the dyeing composition.

In the case of permanent oxidation dyeing or of direct dyeing, the dyeing composition is mixed, preferably at the time of use, with a composition comprising, in a medium acceptable for dyeing, at least one oxidizing agent, this oxidizing agent being present in an amount sufficient to develop a coloring. The mixture obtained is subsequently applied to the keratinous fibers. After a leave-in time of 3 to 50 minutes approximately, preferably 5 to 30 minutes approximately, the keratinous fibers are rinsed, washed with a shampoo, rinsed again and then dried.

The oxidizing composition can also include various adjuvants conventionally used in hair dyeing compositions and as defined above.

The pH of the oxidizing composition including the oxidizing agent is such that, after mixing with the dyeing composition, the pH of the resulting composition applied to keratinous fibers preferably varies between 3 and 12 approximately, and more preferably still between 5 and 11. It can be adjusted to the desired value by means of acidifying or basifying agents commonly used in dyeing keratinous fibers and as defined above.

The composition which is finally applied to the keratinous fibers can be provided in various forms, such as in the form of liquids, creams or gels or in any other form appropriate for carrying out dyeing of keratinous fibers and in particular of human hair.

Another subject matter of the invention is a multi-compartment device or dyeing 'kit' in which a first compartment includes the dyeing composition of the invention and a second compartment includes the oxidizing composition. This device can be equipped with a means allowing the desired mixture to be delivered to the hair, such as the devices disclosed in Patent FR 2 586 913 on behalf of the Applicant Company.

Finally, another subject matter of the invention is the cationic azo dyes of formula (I) or (II) as defined above in which $R_8$ is hydrogen. These compounds can be obtained from the preparation processes described for example in the documents EP 810824, GB 9619573, RO 106572, J. Chem. Res., Synop. (1998), (10), 648–649, DE 19721619, U.S. Pat. No. 5,852,179, Synth. Commun 1999, 29(13), 2271–2276, Org. Lett., 2001, 3, 2583, Org. Lett. 2001, 3, 2757 J. Chem. Soc., Perkin Trans. 1, 1998, 2615–2622 and references obtained from these publications. In particular, the compounds of formula (II) can be obtained in the following manner:

Route 1:

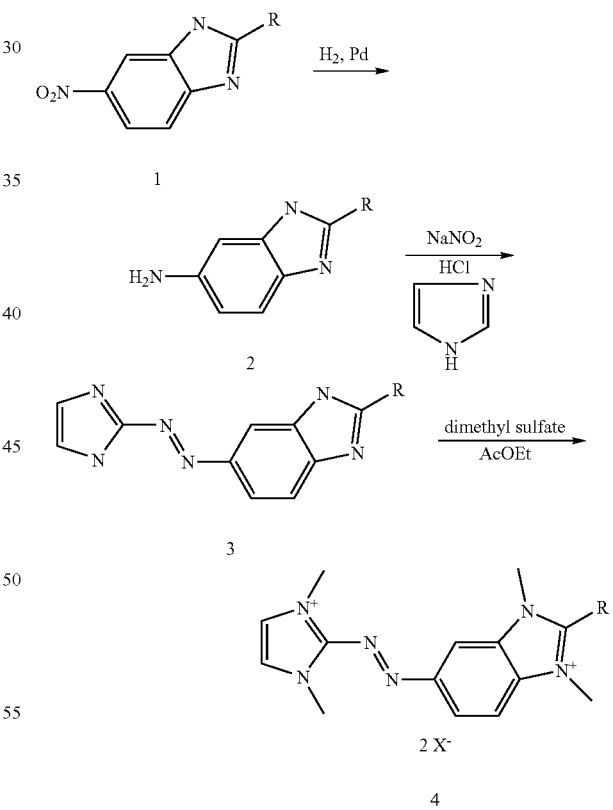

In general, compound 1 is in a first step reduced to compound 2 in the presence of hydrogen under pressure and palladium. This compound subsequently reacts in the presence of sodium nitride to give a diazonium salt which can be fused with the imidazole and thus give compound 3. The double cationization is carried out in the presence of dimethyl sulfate in ethyl acetate to give compound 4.

Route 2:

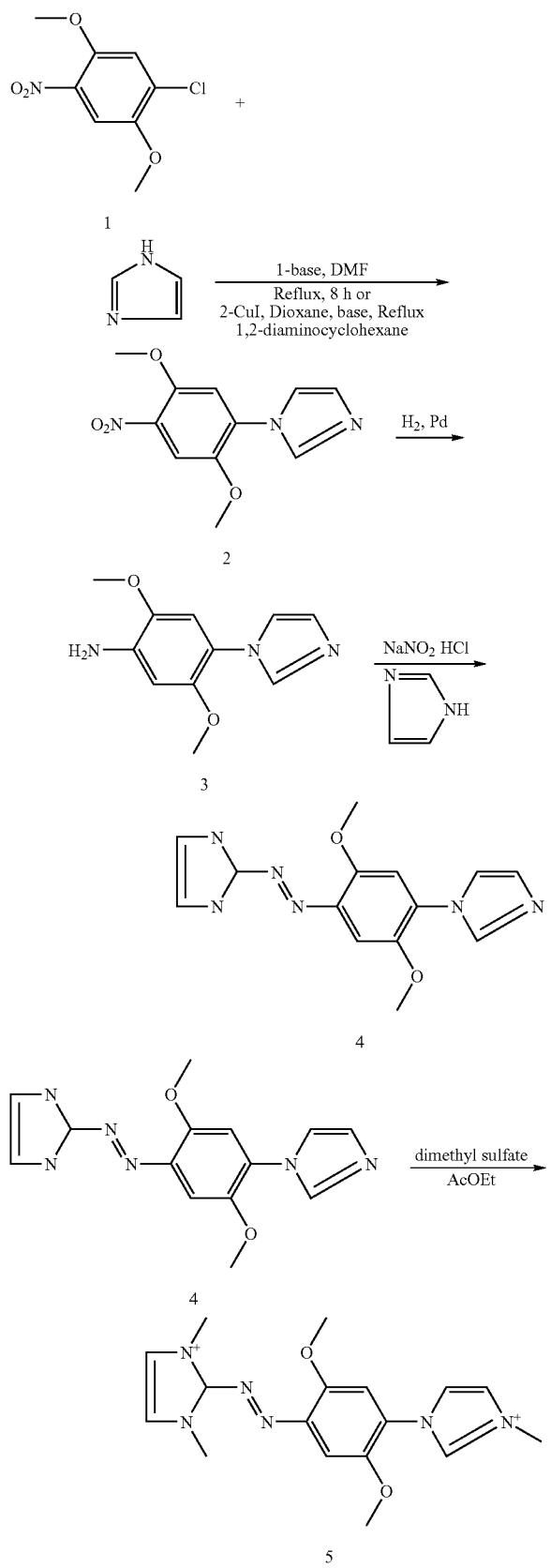

In general, the appropriately chosen compound 1 can be reacted with a 5-membered heteroaromatic system as defined in the claims (here an imidazole) in the presence of a base under reflux. An alternative can be proposed using a copper catalyst, a base, and a ligand, 1,2-diaminocyclohexane under reflux. Compound 3 is obtained by reducing compound 2 using palladium under hydrogen pressure. Compound 3 then reacts in the presence of sodium nitrite to give a diazonium salt which can be fused with the imidazole and thus give compound 4. The double cationization is carried out in the presence of dimethyl sulfate in ethyl acetate to give compound 5.

The following examples serve to illustrate the invention without, however, exhibiting a limiting nature.

EXAMPLES OF SYNTHESIS

Example No. 1

Preparation of a Compound of Formula

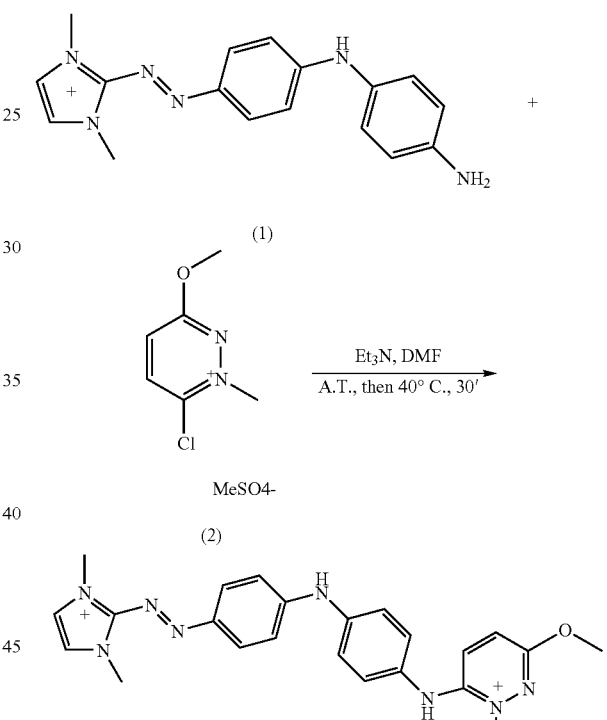

0.05 g of compound (1), 0.04 g of compound (2), 0.3 ml of triethylamine and 0.8 ml of dry DMF are charged to a fully equipped round-bottomed flask. The mixture is left at ambient temperature for 1 hour and then brought to 45° C. The reaction mixture is then filtered through a Büchner funnel. The precipitate is washed with a few drops of ethanol. A volume V of ethyl acetate is then added to the filtered solution. A new precipitate is formed and then filtered through a Büchner funnel. It is then dried under vacuum. After purification, a bright, very dark red powder is obtained. A dye is thus obtained which gives a fuchsia color.

The UV absorption characteristics of this product are as follows:

UV (acetonitrile-water 50/50) $\lambda_{max}$=513 nm

Analyses: $^1$H NMR: (400 MHz-DMSO) ppm: 3.99 (s-3H); 4.02 (s-3H); 4.11 (s-3H); 7.24 (d-2H, J=9.13 Hz);

7.30 (m-3H); 7.45 (d-2H, J=9.75 Hz); 7.63 (s-2H); 8.05 (d-2H, J=12 Hz)

Example No. 2

Preparation of a Compound of Formula 0.05 g of compound (1), 0.037 g of compound (3), 0.3 ml of triethylamine and 0.8 ml of dry DMF are charged to a fully equipped round-bottomed flask. The mixture is left at ambient temperature for 1 hour and then brought to 45° C. The reaction mixture is then filtered through a Büchner funnel. The precipitate is washed with a few drops of ethanol. A volume V of ethyl acetate is then added to the filtered solution. A new precipitate is formed and then filtered through a Büchner funnel. It is then dried under vacuum. After purification, a bright, very dark red powder is obtained.

The UV absorption characteristics of this product are as follows:

UV (acetonitrile-water 50/50) $\lambda_{max}$=516 nm

Analyses: Mass ESI+: m/z=398 [$M^{2+}$] m/z=200 [$M^{2+}$/2+H] $^1$H NMR: (400 MHz-DMSO) ppm: 4.01 (s-6H); 7.09 (m-1H); 7.30 (m-1H); 7.44 (m-5H), 7.74 (s-2H); 8 (m-4H); 8.36 (m-1H); 10.14 (s-2H).

A dye is thus obtained which gives a fuchsia color.

Dyeing Examples

The following dyeing compositions were prepared (contents in mol):

| | |
|---|---|
| Example | 3 |
| Azo dye of example 1 | 5 × 10$^{-4}$ mol |
| Polyethylene glycol 8 EO | 12 g |
| Benzyl alcohol | 10 g |
| Borate buffer q.s. | 100 g |
| pH | 9.05 |

At the time of use, each composition is mixed with an equal weight of 20-volumes hydrogen peroxide (6% by weight).

Each mixture obtained is applied to locks of gray hair comprising 90% permanently waved (BP) or natural (BN) white hair (1 g of lock per 10 g of solution). After allowing the mixture to act for 20 min, the locks are rinsed, washed with a standard shampoo, rinsed again and then dried.

Each lock is evaluated before and after dyeing in the L*a*b* system, by means of a CM 2002 MINOLTA® spectrophotometer (illuminant D65).

In the L*a*b* space, the lightness is indicated by the value L* on a scale from 0 to 100 whereas the chromatic coordinates are expressed by a* and b* which indicate two color axes, a* the red-green axis and b* the yellow-blue axis.

According to this system, the higher the value of L, the lighter and less intense the color. Conversely, the lower the value of L, the darker or more intense the color.

The following dyeing results were obtained.

| | Natural hair | | | Permanently waved hair | | |
|---|---|---|---|---|---|---|
| | L* | a* | b* | L* | a* | b* |
| Example 1 | 19.9 | 6.9 | −2.24 | 20.4 | 4.90 | −3.05 |

What is claimed is:

1. A composition for dyeing keratinous fibers, comprising at least one dicationic monoazo dye chosen from compounds of the following formulae (I) and (II):

$$Z_1\text{—}N\text{=}N\text{—}A_1\text{—}(A_3)_n\text{—}Z_2 \qquad (I)$$

$$Z_1\text{—}N\text{=}N\text{—}A_2 \qquad (II)$$

wherein:

n is equal to 0 or 1, $Z_1$ is a 5- or 6-membered cationic heteroaromatic radical chosen from radicals of formulae (III) and (IV):

wherein:

X is $NR_3$, S or O, Z is $CR_2$ or N, and Y is $CR_4$ or N, with the proviso that:
  when X is $NR_3$ or O and Z is $CR_2$, then Y is $CR_4$ or N,
  when X is S, then Z is N or Y is N,
  when X is S and Z is N, then Y is $CR_4$, $X_1$ is $CR_6$ or N, m is equal to 0, 1, 2 or 3, $R_1$, $R_3$ and $R_5$, which may be identical or different, are each chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen, halogen and sulfur atoms and an $SO_2$ group, with the exception of the carbon atom connected to the nitrogen atom of the ring of formula (III) or (IV); wherein at least one of $R_1$, $R_3$ and $R_5$ does not comprise a peroxide bond or a diazo, nitro or nitroso radical;

$R_2$, $R_4$ and $R_6$, which may be identical or different, are each chosen from a hydrogen atom and linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein at least one of the radicals $R_2$, $R_4$ and $R_6$ does not comprise a peroxide bond or a diazo, nitro or nitroso radical; the radicals $R_2$ and $R_4$ can form together a carbonaceous aromatic ring, and V is an organic or inorganic anion, $A_1$ and $A_3$, which may be identical or different, are each chosen from divalent radicals of formulae (V) and (VI)

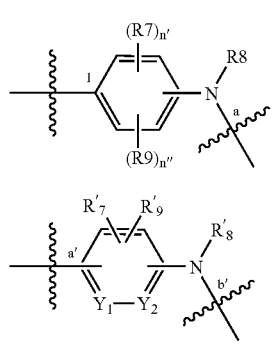

(V)

(VI)

wherein
n' is equal to 0, 1, 2 or 3,
n" is equal to 0 or 1,
$Y_1$–$Y_2$ is C—N or N—N,
when n=0, then the bond a of the group $A_1$ of formula (V) is connected to the functional group $Z_2$ of formula (I) or,
when n=0, then the bond b' of the group $A_1$ of formula (VI) is connected to the functional group $Z_2$ of formula (I),
when n=1, then the bond a of the group $A_1$ of formula (V) is connected to the $C_1$ of the group $A_3$ of formula (V), the bond a of the group $A_3$ of formula (V) being connected to the functional group $Z_2$ of formula (I) or,
when n=1, then the bond a of the group $A_1$ of formula (V) is connected to the carbon carrying the bond a' of the group $A_3$ of formula (VI), the bond b' being connected to the functional group $Z_2$ of formula (I),
when n=1, then the bond b' of the group $A_1$ of formula (VI) is connected to the $C_1$ carbon of the group $A_3$ of formula (V), the bond a being connected to the functional group $Z_2$ of formula (I) or,
when n=1, then the bond b' of the group $A_1$ of formula (VI) is connected to the carbon carrying the bond b' of the group $A_3$ of formula (VI), the bond a' of the group $A_3$ of formula (VI) being connected to the functional group $Z_2$ of formula (I), $R_8$ and $R'_8$, which may be identical or different, are each a noncationic group chosen from a hydrogen atom and linear and branched $C_1$–$C_{10}$ hydrocarbonaceous chains which can form an optionally aromatic 5- to 7-membered carbon ring; it being possible for at least one carbon atom of the hydrocarbonaceous chain to be replaced by at least one entity chosen from oxygen, nitrogen and sulfur atoms and an $SO_2$ group with the exception of the carbon atom connected to the nitrogen atom; wherein at least one of the radicals $R_8$ and $R'_8$ does not comprise a peroxide bond or a diazo, nitro or nitroso radical;

$R_7$, $R_9$, $R'_7$ and $R'_9$, which may be identical or different, are each a cationic group $Z_3$ or a noncationic group chosen from a hydrogen atom and linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein the noncationic group does not comprise a peroxide bond or a diazo, nitro or nitroso radical, provided that only one of the groups $R_7$, $R_9$, $R'_7$ and $R'_9$ is cationic, $R_7$ with $R_8$, or $R'_7$ with $R'_8$ can form together a saturated 5- or 6-membered heterocycle, $Z_3$ is a cationic group of the following formula (VII)

(VII)

wherein:
B is chosen from linear and branched hydrocarbonaceous chains comprising from 1 to 15 carbon atoms, which can form at least one optionally aromatic 3- to 7-membered ring, and at least one carbon atom of the hydrocarbonaceous chain can be replaced by at least one entity chosen from oxygen, nitrogen and sulfur atoms and an $SO_2$ group, with the exception of the carbon atom connected to the nitrogen atom; wherein B does not comprise a peroxide bond or a diazo, nitro or nitroso radical, the radical B is connected to D by any of the atoms of the radical D, n''' is 0 or 1, D is a cationic group chosen from the cationic groups of the following formulae (VIII) and (IX):

(VIII)

(IX)

wherein:
p is 0 or 1;
$T_1$, $T_2$, $T_3$ and $T_4$, which may be identical or different, are each chosen from an oxygen atom; a sulfur atom; a nitrogen atom which is optionally substituted with at least one radical $R_{14}$; and a carbon atom which is optionally substituted with one or two identical or different radicals $R_{14}$;

$T_5$ is chosen from a nitrogen atom and a carbon atom which is optionally substituted with at least one radical $R_{14}$;

$T_6$ is chosen from linear and branched hydrocarbonaceous chains comprising from 1 to 10 carbon atoms, which are optionally aromatic, and at least one carbon atom of the hydrocarbonaceous chain can be replaced by at least one entity chosen from oxygen, nitrogen, halogen, and sulfur atoms and an $SO_2$ group; wherein $T_6$ does not comprise a peroxide bond or a diazo, nitro or nitroso radical;

$T_1$ or $T_5$ can optionally form with $T_6$ a 5- to 7-membered saturated or unsaturated ring, wherein each member of the ring is optionally substituted with one or two identical or different radicals $R_{14}$;

two of the adjacent radicals $T_1$, $T_2$, $T_3$, $T_4$ and $T_5$ can optionally form a 5- to 7-membered ring, wherein each member of the ring is chosen from a carbon atom which is optionally substituted with one or two identical or different radicals $R_{14}$, a nitrogen atom which is optionally substituted with at least one radical $R_{14}$, an oxygen atom, and a sulfur atom;

$R_{10}$, $R_{11}$, $R_{12}$, $R_{13}$ and $R_{14}$, which may be identical or different, are each chosen from a hydrogen atom and linear and branched hydrocarbonaceous chains comprising from 1 to 10 carbon atoms, which are optionally aromatic, and wherein at least one carbon atom of the hydrocarbonaceous chain can be replaced by at least one entity chosen from oxygen, nitrogen, halogen, and sulfur atoms and an $SO_2$ group, and/or can be substituted by, independently of one another, at least one halogen atom; wherein at least one of $R_{10}$, $R_{11}$, $R_{12}$, $R_{13}$ and $R_{14}$ does not comprise a peroxide bond or a diazo, nitro or nitroso radical;

$R_{10}$, $R_{11}$ and $R_{12}$ can also form, in pairs with the quaternary nitrogen atom to which they are attached, at least one ring chosen from 5- to 7-membered saturated rings, wherein each member of the ring is chosen from a carbon atom which is optionally substituted with one or two identical or different radicals $R_{14}$, a nitrogen atom which is optionally substituted with at least one radical $R_{14}$, an oxygen atom, and a sulfur atom, when n'''=0, then the group of formula (IX) can be connected to the compound of formula (V) and (VI) directly by the nitrogen atom of the quaternary ammonium, wherein $R_{13}$ is a single bond, and V' is an organic or inorganic anion, $Z_2$ is chosen from linear and branched $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group, wherein the radical $Z_2$ does not comprise a peroxide bond or a diazo, nitro or nitroso radical; with a proviso that $Z_2$ is not cationic when $R_7$, $R_9$, $R'_7$ or $R'_9$ is cationic, $A_2$ is a radical of formula (X) chosen from carbonaceous aromatic, pyridine and pyridazine radicals substituted with at least one radical chosen from 5-membered cationic heteroaromatic radicals, optionally substituted with at least one noncationic radical $R_{19}$ chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein $R_{19}$ does not comprise a peroxide bond or a diazo, nitro or nitroso radical; or a radical of formula (XI):

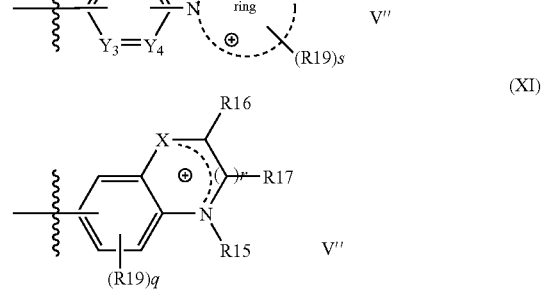

wherein:
r is equal to 0 or 1,
q is equal to 0, 1, 2 or 3,
s is equal to 0, 1, 2, 3, 4 or 5,
t is equal to 0, 1, or 2,
$Y_3$=$Y_4$ is C=C, C=N or N=N,
if r=0, then X is O, S, $NR_{18}$, $CR_{20}$,
if r=1, then X is $CR_{20}$, $R_{15}$ and $R_{18}$, which may be identical or different, are each chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen, halogen and sulfur atoms and an $SO_2$ group, with the exception of the carbon atom connected to the nitrogen atom; wherein at least one of the radicals $R_{15}$, and $R_{18}$ does not comprise a peroxide bond or a diazo, nitro or nitroso radical, $R_{16}$, $R_{17}$, $R_{19}$, $R_{20}$ and $R_{21}$, which may be identical or different, are each chosen from a hydrogen atom and linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein at least one of the radicals $R_{16}$, $R_{17}$, $R_{19}$, $R_{20}$, and $R_{21}$ does not comprise a peroxide bond or a diazo, nitro or nitroso radical, and V''' is an organic or inorganic anion, provided that in formula (I), one of the groups $A_1$, $Z_2$ and $A_3$ is a cationic group.

2. The composition according to claim 1, wherein the radicals $R_1$, $R_3$ and $R_5$, which may be identical or different, are each chosen from $C_1$–$C_4$ alkyl and alkenyl radicals which can be substituted with at least one group chosen from hydroxyl, and optionally substituted amino and carboxyl groups; a phenyl radical which can be substituted with at least one entity chosen from halogen atoms, $C_1$–$C_4$ alkyl, $C_1$–$C_4$ alkoxy, amino, hydroxyl, trifluoromethyl, $C_1$–$C_4$ alkylamino, carboxyl and sulfonyl groups; a benzyl radical which can be substituted with at least one entity chosen from halogen atoms, $C_1$–$C_4$ alkyl, $C_1$–$C_4$ alkoxy, amino and trifluoromethyl groups; a heterocycle chosen from imidazole, thiazole, pyridine and pyrimidine; a radical $(CH_2)_p$—T—$(CH_2)_q$—$V_1$R' wherein p and q, which may be identical or different, are each an integer chosen from 1, 2, and 3, R' is H or methyl, and T and $V_1$, which may be identical or different, are each chosen from an oxygen atom and a radical NR" wherein R" is a hydrogen atom or a methyl group.

3. The composition according to claim 2, wherein $R_1$, $R_3$ and $R_5$ are each chosen from methyl, ethyl, hydroxyethyl, aminoethyl, carboxymethyl, carboxyethyl, phenyl and benzyl radicals; and heterocycles chosen from pyridyl, imidazolyl and pyrimidinyl.

4. The composition according to claim 3, wherein $R_1$ and $R_3$ are chosen from methyl, ethyl, phenyl, hydroxyethyl, aminoethyl, carboxymethyl and carboxyethyl groups.

5. The composition according to claim 1, wherein the radicals $R_2$, $R_4$ and $R_6$, which may be identical or different, are each chosen from a hydrogen atom; an alkyl radical; an alkyl radical substituted with at least one entity chosen from hydroxyl and amino groups and halogen atoms; a phenyl radical which can be substituted with at least one radical chosen from alkyl, hydroxyl, amino, alkoxy, carboxyl, trifluoromethyl and sulfonic radicals; benzyl radicals; benzyl radicals substituted with at least one radical chosen from alkoxy and hydroxyl radicals; a heterocycle chosen from N-pyrrolidinyl, N-piperidinyl, N-morpholine, N-piperazinyl and N-imidazolyl; an alkoxy radical; a phosphonyl radical; a siloxy radical; an amino radical; $C_1$–$C_4$ (di)alkylamino radicals; an acyl radical; an acylamino radical; a sulfonamide radical; a ureido radical; and a sulfonylamino radical.

6. The composition according to claim 5, wherein $R_2$, $R_4$ and $R_6$ are each chosen from a hydrogen atom; an alkyl radical chosen from methyl and ethyl radicals; a substituted alkyl radical chosen from trifluoromethyl; hydroxymethyl, hydroxyethyl, aminomethyl, and aminoethyl radicals; a benzyl radical; a phenyl radical optionally substituted with at least one radical chosen from methyl, hydroxyl, amino and methoxy radicals; 2-methoxybenzyl; 4-methoxybenzyl; 2-hydroxybenzyl; 4-hydroxybenzyl; a heterocycle chosen from pyrrolidinyl and piperidinyl; a methoxy radical; an acyl radical; an amino radical; and $C_1$–$C_4$ (di)alkylamino radicals.

7. The composition according to claim 6, wherein $R_2$, $R_4$ and $R_6$ are each chosen from a hydrogen atom and methyl, ethyl, trifluoromethyl, phenyl, pyrrolidinyl, methoxy, and amino radicals.

8. The composition according to claim 1, wherein $R_8$ and $R'_8$, which may be identical or different, are each chosen from $C_1$–$C_4$ alkyl and alkenyl radicals which can be substituted with a least one radical chosen from hydroxyl, optionally substituted amino and carboxyl radicals; a phenyl radical which can be substituted with at least one entity chosen from halogen atoms, $C_1$–$C_4$ alkyl, $C_1$–$C_4$ alkoxy, amino, hydroxyl, trifluoromethyl, $C_1$–$C_4$ alkylamino, carboxyl and sulfonyl groups; a heterocycle chosen from imidazole, thiazole, pyridine and pyrimidine; a radical $(CH_2)_p$—Tr—$(CH_2)_q$—$V_1$R' wherein p and q, which may be identical or different, are each an integer chosen from 1, 2, and 3, R' is H or methyl, and T and $V_1$, which may be identical or different, are each an oxygen atom or a radical N" wherein R" is a hydrogen atom or a methyl radical.

9. The composition according to claim 8, wherein $R_8$ and $R'_8$ are each chosen from a hydrogen atom, methyl, ethyl, hydroxyethyl, aminoethyl, carboxymethyl, carboxyethyl and phenyl radicals; heterocycles chosen from pyridynyl, imidazolyl and pyrimidinyl.

10. The composition according to claim 1, wherein B is chosen from optionally substituted alkyl radicals chosen from methyl, ethyl, and propyl radicals; hydroxymethyl, hydroxyethyl, aminomethyl, and aminoethyl radicals; a methoxybenzyl radical; a phenyl radical; and a heterocycle chosen from piperazinyl and triazine radicals.

11. The composition according to claim 1, wherein $R_{10}$, $R_{11}$, $R_{12}$, $R_{13}$ and $R_{14}$, which may be identical or different, are each chosen from a hydrogen atom; $C_1$–$C_4$ alkyl and alkenyl radicals which can be substituted with at least one radical chosen from hydroxyl and optionally substituted amino radicals; a phenyl radical which can be substituted with at least one entity chosen from halogen atoms and $C_1$–$C_4$ alkyl, $C_1$–$C_4$ alkoxy, amino, hydroxyl, trifluoromethyl, $C_1$–$C_4$ alkylamino, carboxyl and sulfonyl groups; a benzyl radical which can be substituted with at least one entity chosen from halogen atoms, $C_1$–$C_4$ alkyl, $C_1$–$C_4$ alkoxy, amino and trifluoromethyl groups; $C_1$–$C_4$ (poly)aminoalkyl radicals; a radical $(CH_2)_p$—Tr—$(CH_2)_q$—$V_1$R' wherein p and q, which may be identical or different, are each an integer chosen from 1, 2, and 3, R' is H or methyl, and T and $V_1$, which may be identical of different, are each an oxygen atom or radical NR" wherein R" is chosen from a hydrogen atom and methyl and sulfonyl radicals.

12. The composition according to claim 11, wherein $R_{10}$, $R_{11}$, $R_{12}$, $R_{13}$ and $R_{14}$ are each chosen from ethyl, methyl, isopropyl, hydroxyethyl, aminoethyl, phenyl and benzyl radicals; and heterocycles chosen from pyridynyl, imidazolyl and pyrimidinyl.

13. The composition according to claim 1, wherein $Z_1$ is chosen from imidazolinium, triazolinium, pyridinium and pyridazinium radicals optionally substituted on at least one of the carbon atoms of the ring with at least one radical chosen from methyl, methoxy, carboxyl, amino, phenyl, and pyrrolidine radicals, and on the nitrogen atom with at least one radical chosen from methyl, 2-hydroxyethyl, carboxymethyl and carboxyethyl radicals.

14. The composition according to claim 1, wherein $Z_2$ is chosen from imidazolium, pyridinium, pyridazinium, pyrimidinium and pyrazinium radicals.

15. The composition according to claim 1, wherein $A_2$ is chosen from pyrazolyl, pyrrolyl, imidazolyl, triazolyl and thiadiazolyl radicals, optionally substituted.

16. The composition according to claim 1, wherein $A_1$ and $A_3$, which may be identical or different, are each chosen from aniline, aminopyridinyl and aminopyridazinyl radicals optionally substituted with at least one entity chosen from a hydrogen atom and methyl, ethyl, hydroxymethyl, hydroxyethyl, 1,2-dihydroxyethyl, 1,2-dihydroxypropyl, 2,3-dihydroxypropyl, aminomethyl, aminoethyl and aminopropyl radicals; a trifluoromethyl radical; a heterocycle chosen from N-pyrrolidinyl, N-piperidinyl, N-morpholine, N-piperazinyl and N-imidazolyl; an alkoxy radical; a phosphonyl radical; a siloxy radical; a 1,2-diaminoethyl radical; a 2,3-diaminopropyl radical; an acyl radical; an acylamino radical; a sulfonamide radical; a ureido radical, and a sulfonylamino radical.

17. The composition according to claim 16, wherein $A_1$ and $A_3$ are each chosen from the following pairs ($A_1$, $A_3$): (aniline radical, aniline radical), (aniline radical, aminopyridinyl radical), and (aminopyridinyl radical, aniline radical).

18. The composition according to claim 17, wherein the pair ($A_1$, $A_3$) is a pair (aniline radical, aniline radical)

optionally substituted with a radical chosen from methyl, ethyl, hydroxymethyl, 1,2-dihydroxyethyl, aminomethyl, 2-aminoethyl, 1,2-diaminoethyl, 2,3-diaminopropyl, pyrrolidinyl, piperidinyl, methoxy, amino, methylamino, dimethylamino, and 2-hydroxyethylamino radicals.

19. The composition according to claim 1, wherein, in formula (I), $Z_1$ is an imidazolium group, n is equal to 1, the pair $(A_1, A_3)$ is a pair (aniline radical, aniline radical) and $Z_2$ is chosen from imidazolium, pyridinium, pyridazinium, pyrimidinium and pyrazinium radicals.

20. The composition according to claim 1, wherein the azo dye of formula (I) is chosen from

| Compound | $Z_1$ | $A_1$ | $A_3$ | n | $Z_2$ |
|---|---|---|---|---|---|
| 1 | 2-imidazolinium | phenyl-NH | | 0 | 2-imidazolinium |
| 2 | 2-imidazolinium | phenyl-NH | phenyl-NH | 1 | 2-imidazolinium |
| 3 | 2-imidazolinium | pyridyl-NH | | 0 | 2-imidazolinium |
| 4 | 2-imidazolinium | phenyl-NH | pyridyl-NH | 1 | 2-imidazolinium |
| 5 | 2-imidazolinium | 2-OMe-phenyl-NH | | 0 | 2-imidazolinium |
| 6 | 2-imidazolinium | 2-OMe-phenyl-NH | phenyl-NH | 1 | 2-imidazolinium |
| 7 | 2-imidazolinium | 3-OMe-pyridyl-NH | | 0 | 2-imidazolinium |
| 8 | 2-imidazolinium | 2-OMe-phenyl-NH | pyridyl-NH | 1 | 2-imidazolinium |
| 9 | 2-imidazolinium | 2,5-diOMe-phenyl-NH | | 0 | 2-imidazolinium |

-continued

| Compound | $Z_1$ | $A_1$ | $A_3$ | n | $Z_2$ |
|---|---|---|---|---|---|
| 10 | 2-imidazolinium | 2,5-dimethoxyphenyl-NH- | 1,4-phenyl-NH- | 1 | 2-imidazolinium |
| 11 | 2-imidazolinium | 3,6-dimethoxypyridin-2-yl-NH- | | 0 | 2-imidazolinium |
| 12 | 2-imidazolinium | 2,5-dimethoxyphenyl-NH- | pyridin-2-yl-NH- | 1 | 2-imidazolinium |
| 13 | 2-imidazolinium | 2-methylphenyl-NH- | | 0 | 2-imidazolinium |
| 14 | 2-imidazolinium | 2-methylphenyl-NH- | 1,4-phenyl-NH- | 1 | 2-imidazolinium |
| 15 | 2-imidazolinium | 4-methylpyridin-2-yl-NH- | | 0 | 2-imidazolinium |
| 16 | 2-imidazolinium | 2-methylphenyl-NH- | pyridin-2-yl-NH- | 1 | 2-imidazolinium |
| 17 | 2-triazolinium | 1,4-phenyl-NH- | | 0 | 2-imidazolinium |
| 18 | 2-triazolinium | pyridin-2-yl-NH- | 1,4-phenyl-NH- | 1 | 2-imidazolinium |
| 19 | 2-triazolinium | pyridin-2-yl-NH- | | 0 | 2-imidazolinium |

| Compound | $Z_1$ | $A_1$ | $A_3$ | n | $Z_2$ |
|---|---|---|---|---|---|
| 20 | 2-triazolinium | 1,4-phenylene-NH- | 5-(2-amino)pyridinyl | 1 | 2-imidazolinium |
| 21 | 2-triazolinium | 3-methoxy-1,4-phenylene-NH- | | 0 | 2-imidazolinium |
| 22 | 2-triazolinium | 3-methoxy-1,4-phenylene-NH- | 1,4-phenylene-NH- | 1 | 2-imidazolinium |
| 23 | 2-triazolinium | 3-methoxy-5-pyridinyl-NH- | | 0 | 2-imidazolinium |
| 24 | 2-triazolinium | 3-methoxy-1,4-phenylene-NH- | 5-(2-amino)pyridinyl | 1 | 2-imidazolinium |
| 25 | 2-triazolinium | 2,5-dimethoxy-1,4-phenylene-NH- | | 0 | 2-imidazolinium |
| 26 | 2-triazolinium | 2,5-dimethoxy-1,4-phenylene-NH- | 1,4-phenylene-NH- | 1 | 2-imidazolinium |
| 27 | 2-triazolinium | 3,6-dimethoxy-2-aminopyridinyl | | 0 | 2-imidazolinium |
| 28 | 2-triazolinium | 2,5-dimethoxy-1,4-phenylene-NH- | 5-(2-amino)pyridinyl | 1 | 2-imidazolinium |

-continued

| Compound | $Z_1$ | $A_1$ | $A_3$ | n | $Z_2$ |
|---|---|---|---|---|---|
| 29 | 2-triazolinium | 3-methyl-4-aminophenyl | | 0 | 2-imidazolinium |
| 30 | 2-triazolinium | 3-methyl-4-aminophenyl | 4-aminophenyl | 1 | 2-imidazolinium |
| 31 | 2-triazolinium | 4-methyl-2-aminopyridinyl | | 0 | 2-imidazolinium |
| 32 | 2-triazolinium | 3-methyl-4-aminophenyl | 2-aminopyridinyl | 1 | 2-imidazolinium |
| 33 | 3-pyridinium | 4-aminophenyl | | 0 | 2-imidazolinium |
| 34 | 3-pyridinium | 4-aminophenyl | 4-aminophenyl | 1 | 2-imidazolinium |
| 35 | 3-pyridinium | 2-aminopyridinyl | | 0 | 2-imidazolinium |
| 36 | 3-pyridinium | 4-aminophenyl | 2-aminopyridinyl | 1 | 2-imidazolinium |
| 37 | 3-pyridinium | 2-methoxy-4-aminophenyl | | 0 | 2-imidazolinium |
| 38 | 3-pyridinium | 2-methoxy-4-aminophenyl | 4-aminophenyl | 1 | 2-imidazolinium |

-continued

| Compound | Z₁ | A₁ | A₃ | n | Z₂ |
|---|---|---|---|---|---|
| 39 | 3-pyridinium | pyridine with OMe and NH substituents | | 0 | 2-imidazolinium |
| 40 | 3-pyridinium | benzene with OMe and NH substituents | pyridine with NH substituent | 1 | 2-imidazolinium |
| 41 | 3-pyridinium | benzene with OMe, MeO and NH substituents | | 0 | 2-imidazolinium |
| 42 | 3-pyridinium | benzene with OMe, MeO and NH substituents | benzene with NH substituent | 1 | 2-imidazolinium |
| 43 | 3-pyridinium | pyridine with OMe, MeO and NH substituents | | 0 | 2-imidazolinium |
| 44 | 3-pyridinium | benzene with OMe, MeO and NH substituents | pyridine with NH substituent | 1 | 2-imidazolinium |
| 45 | 3-pyridinium | benzene with Me and NH substituents | | 0 | 2-imidazolinium |
| 46 | 3-pyridinium | benzene with Me and NH substituents | benzene with NH substituent | 1 | 2-imidazolinium |
| 47 | 3-pyridinium | pyridine with Me and NH substituents | | 0 | 2-imidazolinium |

-continued

| Compound | Z₁ | A₁ | A₃ | n | Z₂ |
|---|---|---|---|---|---|
| 48 | 3-pyridinium | (methyl-substituted phenyl-NH-) | (pyridine-NH-) | 1 | 2-imidazolinium |
| 49 | 2-imidazolinium | (phenyl-NH-) | | 0 | 2-pyridinium |
| 50 | 2-imidazolinium | (OMe-substituted phenyl-NH-) | | 0 | 2-pyridinium |
| 51 | 2-imidazolinium | (pyridine-NH-) | | 0 | 2-pyridinium |
| 52 | 2-imidazolinium | (OMe-substituted pyridine-NH-) | | 0 | 2-pyridinium |
| 53 | 2-imidazolinium | (OMe-substituted phenyl-NH-) | (phenyl-NH-) | 1 | 2-pyridinium |
| 54 | 2-imidazolinium | (di-OMe-substituted phenyl-NH-) | | 0 | 2-pyridinium |
| 55 | 2-imidazolinium | (OMe-substituted phenyl-NH-) | (pyridine-NH-) | 1 | 2-pyridinium |
| 56 | 2-imidazolinium | (di-OMe-substituted pyridine-NH-) | | 0 | 2-pyridinium |

-continued

| Compound | $Z_1$ | $A_1$ | $A_3$ | n | $Z_2$ |
|---|---|---|---|---|---|
| 57 | 2-imidazolinium | 2,5-dimethoxy-1,4-phenylene with NH | 1,4-phenylene with NH | 1 | 2-pyridinium |
| 58 | 2-imidazolinium | 2-methyl-1,4-phenylene with NH | | 0 | 2-pyridinium |
| 59 | 2-imidazolinium | 2-methyl-1,4-phenylene with NH | 1,4-phenylene with NH | 1 | 2-pyridinium |
| 60 | 2-imidazolinium | 4-methyl-pyridine-2,5-diyl with NH | | 0 | 2-pyridinium |
| 61 | 2-imidazolinium | 2-methyl-1,4-phenylene with NH | pyridine-2,5-diyl with NH | 1 | 2-pyridinium |
| 62 | 2-triazolinium | 1,4-phenylene with NH | | 0 | 2-pyridinium |
| 63 | 2-triazolinium | 1,4-phenylene with NH | 1,4-phenylene with NH | 1 | 2-pyridinium |
| 64 | 2-triazolinium | pyridine-2,5-diyl with NH | | 0 | 2-pyridinium |
| 65 | 2-triazolinium | 1,4-phenylene with NH | pyridine-2,5-diyl with NH | 1 | 2-pyridinium |
| 66 | 2-triazolinium | 2-methoxy-1,4-phenylene with NH | | 0 | 2-pyridinium |

-continued

| Compound | $Z_1$ | $A_1$ | $A_3$ | n | $Z_2$ |
|---|---|---|---|---|---|
| 67 | 2-triazolinium | 2-OMe-phenyl-NH- | phenyl-NH- | 1 | 2-pyridinium |
| 68 | 2-triazolinium | 3-OMe-pyridin-2-yl-NH- | | 0 | 2-pyridinium |
| 69 | 2-triazolinium | 2-OMe-phenyl-NH- | pyridin-2-yl-NH- | 1 | 2-pyridinium |
| 70 | 2-triazolinium | 2,5-diOMe-phenyl-NH- | | 0 | 2-pyridinium |
| 71 | 2-triazolinium | 2,5-diOMe-phenyl-NH- | phenyl-NH- | 1 | 2-pyridinium |
| 72 | 2-triazolinium | 3,6-diOMe-pyridin-2-yl-NH- | | 0 | 2-pyridinium |
| 73 | 2-triazolinium | 2,5-diOMe-phenyl-NH- | pyridin-2-yl-NH- | 1 | 2-pyridinium |
| 74 | 2-triazolinium | 2-Me-phenyl-NH- | | 0 | 2-pyridinium |
| 75 | 2-triazolinium | 2-Me-phenyl-NH- | phenyl-NH- | 1 | 2-pyridinium |

-continued

| Compound | $Z_1$ | $A_1$ | $A_3$ | n | $Z_2$ |
|---|---|---|---|---|---|
| 76 | 2-triazolinium | 4-methyl-pyridine-2,5-diyl (NH-linked) | | 0 | 2-pyridinium |
| 77 | 2-triazolinium | 4-methyl-phenylene (NH-linked) | pyridine-2,5-diyl (NH-linked) | 1 | 2-pyridinium |
| 78 | 3-pyridinium | phenylene (NH-linked) | | 0 | 2-pyridinium |
| 79 | 3-pyridinium | phenylene (NH-linked) | phenylene (NH-linked) | 1 | 2-pyridinium |
| 80 | 3-pyridinium | pyridine-2,5-diyl (NH-linked) | | 0 | 2-pyridinium |
| 81 | 3-pyridinium | phenylene (NH-linked) | pyridine-2,5-diyl (NH-linked) | 1 | 2-pyridinium |
| 82 | 3-pyridinium | 2-OMe-phenylene (NH-linked) | | 0 | 2-pyridinium |
| 83 | 3-pyridinium | 2-OMe-phenylene (NH-linked) | phenylene (NH-linked) | 1 | 2-pyridinium |
| 84 | 3-pyridinium | 3-OMe-pyridine-2,5-diyl (NH-linked) | | 0 | 2-pyridinium |
| 85 | 3-pyridinium | 2-OMe-phenylene (NH-linked) | pyridine-2,5-diyl (NH-linked) | 1 | 2-pyridinium |

-continued

| Compound | $Z_1$ | $A_1$ | $A_3$ | n | $Z_2$ |
|---|---|---|---|---|---|
| 86 | 3-pyridinium | 2,5-dimethoxy-phenyl-NH (with OMe, MeO substituents) | | 0 | 2-pyridinium |
| 87 | 3-pyridinium | 2,5-dimethoxy-phenyl-NH | phenyl-NH | 1 | 2-pyridinium |
| 88 | 3-pyridinium | 3,6-dimethoxy-pyridyl-NH | | 0 | 2-pyridinium |
| 89 | 3-pyridinium | 2,5-dimethoxy-phenyl-NH | pyridyl-NH | 1 | 2-pyridinium |
| 90 | 3-pyridinium | 2-methylphenyl-NH | | 0 | 2-pyridinium |
| 91 | 3-pyridinium | 2-methylphenyl-NH | phenyl-NH | 1 | 2-pyridinium |
| 92 | 3-pyridinium | 4-methylpyridyl-NH | | 0 | 2-pyridinium |
| 93 | 3-pyridinium | 2-methylphenyl-NH | pyridyl-NH | 1 | 2-pyridinium |
| 94 | 2-imidazolinium | phenyl-NH | | 0 | 3-pyridazinium |

-continued

| Compound | Z₁ | A₁ | A₃ | n | Z₂ |
|---|---|---|---|---|---|
| 95 | 2-imidazolinium | 2-OMe, 4-NH phenyl |  | 0 | 3-pyridazinium |
| 96 | 2-imidazolinium | 5-(pyridin-2-ylamino) |  | 0 | 3-pyridazinium |
| 97 | 2-imidazolinium | 3-OMe-pyridin-2-ylamino |  | 0 | 3-pyridazinium |
| 98 | 2-imidazolinium | 2-OMe, 4-NH phenyl | 4-NH phenyl | 1 | 3-pyridazinium |
| 99 | 2-imidazolinium | 2-OMe, 4-NH phenyl | 5-(pyridin-2-ylamino) | 1 | 3-pyridazinium |
| 100 | 2-imidazolinium | 2,5-diOMe, 4-NH phenyl |  | 0 | 3-pyridazinium |
| 101 | 2-imidazolinium | 2,5-diOMe, 4-NH phenyl | 4-NH phenyl | 1 | 3-pyridazinium |
| 102 | 2-imidazolinium | 3,6-diOMe-pyridin-2-ylamino |  | 0 | 3-pyridazinium |
| 103 | 2-imidazolinium | 2,5-diOMe, 4-NH phenyl | 5-(pyridin-2-ylamino) | 1 | 3-pyridazinium |

-continued

| Compound | $Z_1$ | $A_1$ | $A_3$ | n | $Z_2$ |
|---|---|---|---|---|---|
| 104 | 2-imidazolinium | methyl-substituted phenyl-NH- | | 0 | 3-pyridazinium |
| 105 | 2-imidazolinium | methyl-substituted phenyl-NH- | phenyl-NH- | 1 | 3-pyridazinium |
| 106 | 2-imidazolinium | methyl-substituted pyridyl-NH- | | 0 | 3-pyridazinium |
| 107 | 2-imidazolinium | methyl-substituted phenyl-NH- | pyridyl-NH- | 1 | 3-pyridazinium |
| 108 | 2-triazolinium | phenyl-NH- | | 0 | 3-pyridazinium |
| 109 | 2-triazolinium | phenyl-NH- | phenyl-NH- | 1 | 3-pyridazinium |
| 110 | 2-triazolinium | pyridyl-NH- | | 0 | 3-pyridazinium |
| 111 | 2-triazolinium | phenyl-NH- | pyridyl-NH- | 1 | 3-pyridazinium |
| 112 | 2-triazolinium | OMe-substituted phenyl-NH- | | 0 | 3-pyridazinium |
| 113 | 2-triazolinium | OMe-substituted phenyl-NH- | phenyl-NH- | 1 | 3-pyridazinium |

-continued

| Compound | $Z_1$ | $A_1$ | $A_3$ | n | $Z_2$ |
|---|---|---|---|---|---|
| 114 | 2-triazolinium | 3-OMe, 2-NH pyridine | | 0 | 3-pyridazinium |
| 115 | 2-triazolinium | 2-OMe, 4-NH phenyl | 5-substituted 2-NH pyridine | 1 | 3-pyridazinium |
| 116 | 2-triazolinium | 2-OMe, 5-OMe, 4-NH phenyl | | 0 | 3-pyridazinium |
| 117 | 2-triazolinium | 2-OMe, 5-OMe, 4-NH phenyl | 4-NH phenyl | 1 | 3-pyridazinium |
| 118 | 2-triazolinium | 3-OMe, 6-OMe, 2-NH pyridine | | 0 | 3-pyridazinium |
| 119 | 2-triazolinium | 2-OMe, 5-OMe, 4-NH phenyl | 5-substituted 2-NH pyridine | 1 | 3-pyridazinium |
| 120 | 2-triazolinium | 3-Me, 4-NH phenyl | | 0 | 3-pyridazinium |
| 121 | 2-triazolinium | 3-Me, 4-NH phenyl | 4-NH phenyl | 1 | 3-pyridazinium |
| 122 | 2-triazolinium | 4-Me, 2-NH pyridine | | 0 | 3-pyridazinium |

-continued

| Compound | $Z_1$ | $A_1$ | $A_3$ | n | $Z_2$ |
|---|---|---|---|---|---|
| 123 | 2-triazolinium | methyl-substituted phenyl-NH- | pyridyl-NH- | 1 | 3-pyridazinium |
| 124 | 3-pyridinium | phenyl-NH- | | 0 | 3-pyridazinium |
| 125 | 3-pyridinium | phenyl-NH- | phenyl-NH- | 1 | 3-pyridazinium |
| 126 | 3-pyridinium | pyridyl-NH- | | 0 | 3-pyridazinium |
| 127 | 3-pyridinium | phenyl-NH- | pyridyl-NH- | 1 | 3-pyridazinium |
| 128 | 3-pyridinium | 2-OMe-phenyl-NH- | | 0 | 3-pyridazinium |
| 129 | 3-pyridinium | 2-OMe-phenyl-NH- | phenyl-NH- | 1 | 3-pyridazinium |
| 130 | 3-pyridinium | 3-OMe-pyridyl-NH- | | 0 | 3-pyridazinium |
| 131 | 3-pyridinium | 2-OMe-phenyl-NH- | pyridyl-NH- | 1 | 3-pyridazinium |
| 132 | 3-pyridinium | 2,5-di-OMe-phenyl-NH- | | 0 | 3-pyridazinium |

-continued
| Compound | $Z_1$ | $A_1$ | $A_3$ | n | $Z_2$ |
|---|---|---|---|---|---|
| 133 | 3-pyridinium | 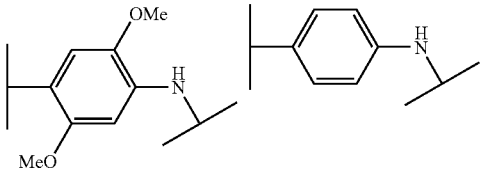 |  | 1 | 3-pyridazinium |
| 134 | 3-pyridinium | 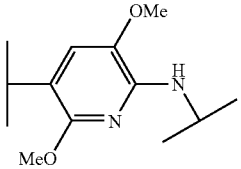 | | 0 | 3-pyridazinium |
| 135 | 3-pyridinium | 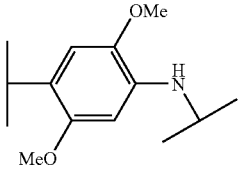 |  | 1 | 3-pyridazinium |
| 136 | 3-pyridinium | 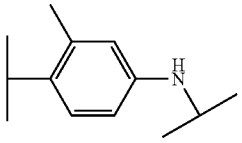 | | 0 | 3-pyridazinium |
| 137 | 3-pyridinium | 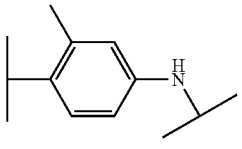 |  | 1 | 3-pyridazinium |
| 138 | 3-pyridinium | 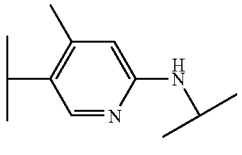 | | 0 | 3-pyridazinium |
| 139 | 3-pyridinium | 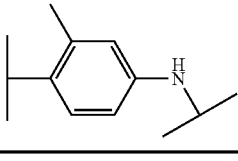 |  | 1 | 3-pyridazinium. |
21. The composition according to claim 20, wherein the azo dye of formula (I) is chosen from:
| Compound | $Z_1$ | $A_1$ | $A_3$ | n | $Z_2$ |
|---|---|---|---|---|---|
| 1 | 2-imidazolinium | 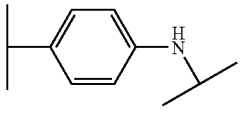 | | 0 | 2-imidazolinium |

| Compound | Z₁ | A₁ | A₃ | n | Z₂ |
|---|---|---|---|---|---|
| 2 | 2-imidazolinium | phenyl-NH- | phenyl-NH- | 1 | 2-imidazolinium |
| 3 | 2-imidazolinium | pyridyl-NH- | | 0 | 2-imidazolinium |
| 4 | 2-imidazolinium | phenyl-NH- | pyridyl-NH- | 1 | 2-imidazolinium |
| 9 | 2-imidazolinium | 2,5-(MeO)₂-phenyl-NH- | | 0 | 2-imidazolinium |
| 10 | 2-imidazolinium | 2,5-(MeO)₂-phenyl-NH- | phenyl-NH- | 1 | 2-imidazolinium |
| 11 | 2-imidazolinium | (MeO)₂-pyridyl-NH- | | 0 | 2-imidazolinium |
| 12 | 2-imidazolinium | 2,5-(MeO)₂-phenyl-NH- | pyridyl-NH- | 1 | 2-imidazolinium |
| 13 | 2-imidazolinium | methyl-phenyl-NH- | | 0 | 2-imidazolinium |
| 14 | 2-imidazolinium | methyl-phenyl-NH- | phenyl-NH- | 1 | 2-imidazolinium |
| 17 | 2-triazolinium | phenyl-NH- | | 0 | 2-imidazolinium |

-continued
| Compound | $Z_1$ | $A_1$ | $A_3$ | n | $Z_2$ |
|---|---|---|---|---|---|
| 18 | 2-triazolinium | 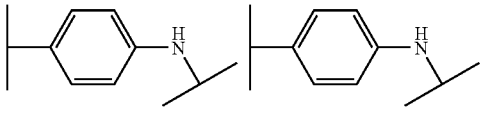 | 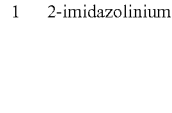 | 1 | 2-imidazolinium |
| 25 | 2-triazolinium | 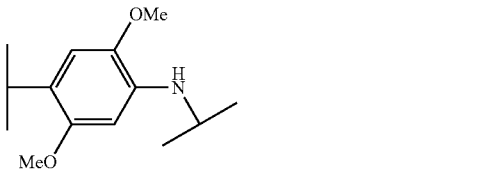 | | 0 | 2-imidazolinium |
| 26 | 2-triazolinium | 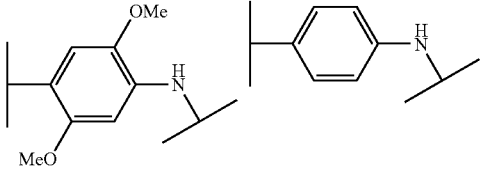 | 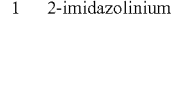 | 1 | 2-imidazolinium |
| 29 | 2-triazolinium | 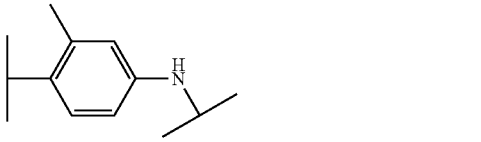 | | 0 | 2-imidazolinium |
| 30 | 2-triazolinium | 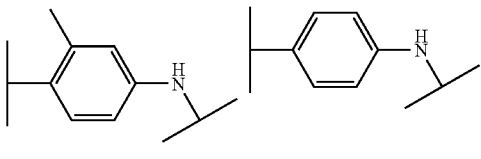 | 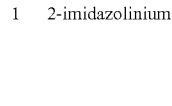 | 1 | 2-imidazolinium |
| 34 | 3-pyridinium | 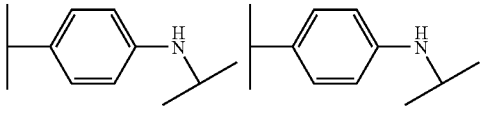 | 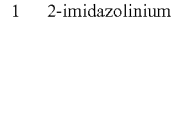 | 1 | 2-imidazolinium |
| 41 | 3-pyridinium | 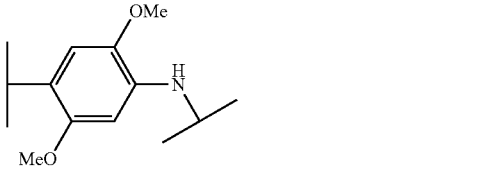 | | 0 | 2-imidazolinium |
| 45 | 3-pyridinium | 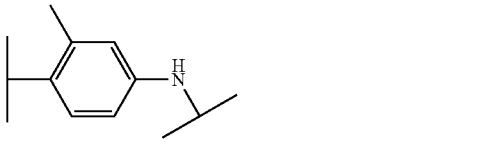 | | 0 | 2-imidazolinium |
| 49 | 2-imidazolinium | 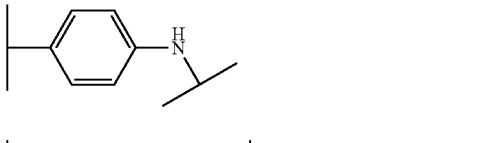 | | 0 | 2-pyridinium |
| 50 | 2-imidazolinium | 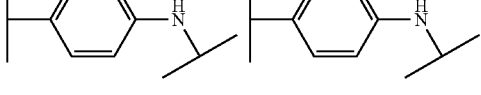 |  | 1 | 2-pyridinium |

-continued
| Compound | $Z_1$ | $A_1$ | $A_3$ | n | $Z_2$ |
|---|---|---|---|---|---|
| 51 | 2-imidazolinium | 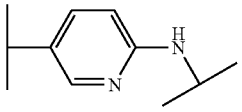 | | 0 | 2-pyridinium |
| 54 | 2-imidazolinium | 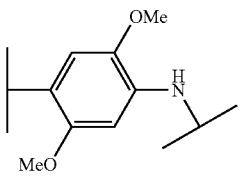 | | 0 | 2-pyridinium |
| 61 | 2-imidazolinium | 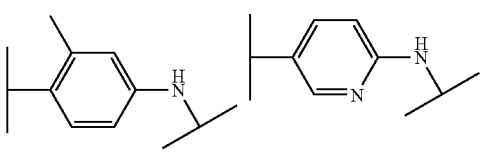 | 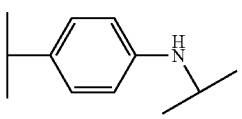 | 1 | 2-pyridinium |
| 78 | 3-pyridinium | 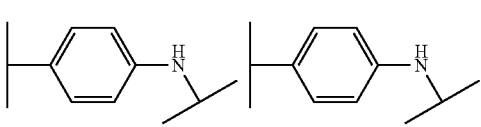 | | 0 | 2-pyridinium |
| 79 | 3-pyridinium | 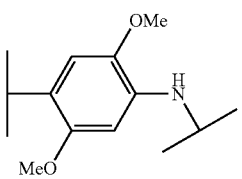 | 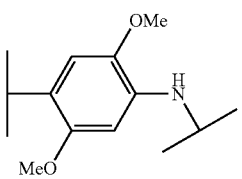 | 1 | 2-pyridinium |
| 86 | 3-pyridinium | 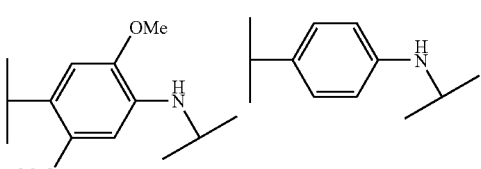 | | 0 | 2-pyridinium |
| 87 | 3-pyridinium | 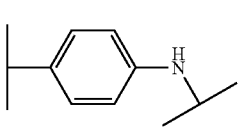 | 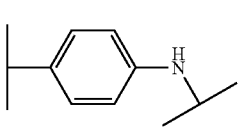 | 1 | 2-pyridinium |
| 94 | 2-imidazolinium | 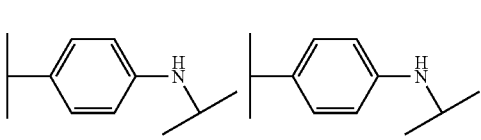 | | 0 | 3-pyridazinium |
| 95 | 2-imidazolinium | 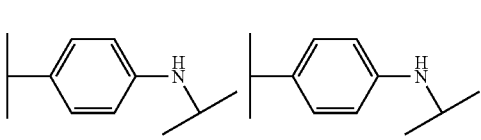 | 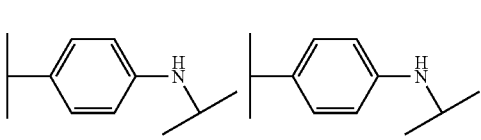 | 1 | 3-pyridazinium |
| 100 | 2-imidazolinium | 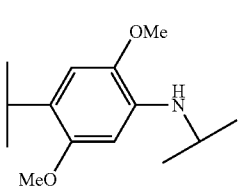 | | 0 | 3-pyridazinium |

-continued

| Compound | $Z_1$ | $A_1$ | $A_3$ | n | $Z_2$ |
|---|---|---|---|---|---|
| 101 | 2-imidazolinium | 2,5-dimethoxy-phenyl-NH- | phenyl-NH- | 1 | 3-pyridazinium |
| 105 | 2-imidazolinium | 2-methyl-phenyl-NH- | phenyl-NH- | 1 | 3-pyridazinium |
| 109 | 2-triazolinium | phenyl-NH- | phenyl-NH- | 1 | 3-pyridazinium |
| 116 | 2-triazolinium | 2,5-dimethoxy-phenyl-NH- |  | 0 | 3-pyridazinium |
| 121 | 2-triazolinium | 2-methyl-phenyl-NH- | phenyl-NH- | 1 | 3-pyridazinium |
| 124 | 3-pyridinium | phenyl-NH- |  | 0 | 3-pyridazinium |
| 125 | 3-pyridinium | phenyl-NH- | phenyl-NH- | 1 | 3-pyridazinium |
| 130 | 3-pyridinium | 3-methoxy-pyridin-2-yl-NH- |  | 0 | 3-pyridazinium |
| 131 | 3-pyridinium | 2-methoxy-phenyl-NH- | pyridin-2-yl-NH- | 1 | 3-pyridazinium |
| 132 | 3-pyridinium | 2,5-dimethoxy-phenyl-NH- |  | 0 | 3-pyridazinium |

-continued

| Compound | $Z_1$ | $A_1$ | $A_3$ | n | $Z_2$ |
|---|---|---|---|---|---|
| 133 | 3-pyridinium | (2,5-dimethoxyphenyl-NH) | (phenyl-NH) | 1 | 3-pyridazinium |
| 136 | 3-pyridinium | (methylphenyl-NH) | | 0 | 3-pyridazinium |
| 137 | 3-pyridinium | (methylphenyl-NH) | (phenyl-NH) | 1 | 3-pyridazinium. |

22. The composition according to claim 1, further comprising at least one oxidation base.

23. The composition according to claim 22, wherein the at least one oxidation base is chosen from para-phenylenediamines, bisphenylalkylenediamines, para-aminophenols, ortho-aminophenols, heterocyclic bases, and acid addition salts thereof.

24. The composition according to claim 22, wherein the at least one oxidation base is present in an amount ranging from 0.001% to 10% by weight relative to the total weight of the composition.

25. The composition according to claim 24, wherein said at least one oxidation base is present in an amount ranging from 0.005% to 6% by weight relative to the total weight of the composition.

26. The composition according to claim 1, further comprising at least one coupler.

27. The composition according to claim 26, wherein the at least one coupler is chosen from meta-phenylenediamines, meta-aminophenols, meta-diphenols, naphthalene couplers and heterocyclic couplers and acid addition salts thereof.

28. The composition according to claim 1, further comprising at least one oxidizing agent.

29. The composition according to claim 28, wherein said at least one oxidizing agent is hydrogen peroxide.

30. The composition according to claim 1, wherein the keratinous fibers are hair.

31. A process for oxidation dyeing of keratinous fibers, comprising applying to the keratinous fiber a dyeing composition comprising at least one dicationic monoazo dye chosen from compounds of the following formulae (I) and (II):

$$Z_1-N=N-A_1-(A_3)_n-Z_2 \quad (I)$$

$$Z_1-N=N-A_2 \quad (II)$$

wherein:

n is equal to 0 or 1, $Z_1$ is a 5- or 6-membered cationic heteroaromatic radical chosen from radicals of formulae (III) and (IV):

$$\text{(III)}$$

$$\text{(IV)}$$

wherein:

X is $NR_3$, S or O, Z is $CR_2$ or N, and Y is $CR_4$ or N, with the proviso that:
when X is $NR_3$ or O and Z is $CR_2$, then Y is $CR_4$ or N,
when X is S, then Z is N or Y is N,
when X is S and Z is N, then Y is $CR_4$, $X_1$ is $CR_6$ or N, m is equal to 0, 1, 2 or 3, $R_1$, $R_3$ and $R_5$, which may be identical or different, are each chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen, halogen and sulfur atoms and an $SO_2$ group, with the exception of the carbon atom connected to the nitrogen atom of the ring of formula (III) or (IV); wherein at least one of $R_1$, $R_3$ and $R_5$ does not comprise a peroxide bond or a diazo, nitro or nitroso radical;

$R_2$, $R_4$ and $R_6$, which may be identical or different, are each chosen from a hydrogen atom and linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein at least one of the radicals $R_2$, $R_4$ and $R_6$ does not comprise a peroxide bond or a diazo, nitro or nitroso radical; the radicals $R_2$ and $R_4$ can form together a carbonaceous aromatic ring, and V is an organic or inorganic anion, $A_1$ and $A_3$, which may be identical or different, are each chosen from divalent radicals of formulae (V) and (VI)

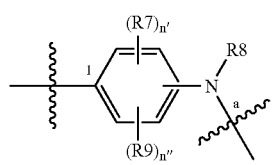
(V)

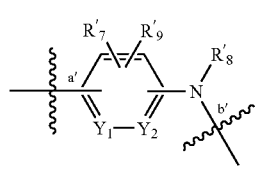
(VI)

wherein
n' is equal to 0, 1, 2 or 3,
n'' is equal to 0 or 1,
$Y_1$–$Y_2$ is C—N or —N,
when n=0, then the bond a of the group $A_1$ of formula (V) is connected to the functional group $Z_2$ of formula (I) or,
when n=0, then the bond b' of the group $A_1$ of formula (VI) is connected to the functional group $Z_2$ of formula (I),
when n=1, then the bond a of the group $A_1$ of formula (V) is connected to the $C_1$ of the group $A_3$ of formula (V), the bond a of the group $A_3$ of formula (V) being connected to the functional group $Z_2$ of formula (I) or,
when n=1, then the bond a of the group $A_1$ of formula (V) is connected to the carbon carrying the bond a' of the group $A_3$ of formula (VI), the bond b' being connected to the functional group $Z_2$ of formula (I),
when n=1, then the bond b' of the group $A_1$ of formula (VI) is connected to the $C_1$ carbon of the group $A_3$ of formula (V), the bond a being connected to the functional group $Z_2$ of formula (I) or,
when n=1, then the bond b' of the group $A_1$ of formula (VI) is connected to the carbon carrying the bond a' of the group $A_3$ of formula (VI), the bond b' of the group $A_3$ of formula (VI) being connected to the functional group $Z_2$ of formula (I),
$R_8$ and $R'_8$, which may be identical or different, are each a noncationic group chosen from a hydrogen atom and linear and branched $C_1$–$C_{10}$ hydrocarbonaceous chains which can form an optionally aromatic 5- to 7-membered carbon ring; it being possible for at least one carbon atom of the hydrocarbonaceous chain to be replaced by at least one entity chosen from oxygen, nitrogen and sulfur atoms and an $SO_2$ group with the exception of the carbon atom connected to the nitrogen atom wherein at least one of the radicals $R_8$ and $R'_8$ does not comprise a peroxide bond or a diazo, nitro or nitroso radical;

$R_7$, $R_9$, $R'_7$ and $R'_9$, which may be identical or different, are each a cationic group $Z_3$ or a noncationic group chosen from a hydrogen atom and linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein the noncationic group does not comprise a peroxide bond or a diazo, nitro or nitroso radical, provided that only one of the groups $R_7$, $R_9$, $R'_7$ and $R'_9$ is cationic, $R_7$ with $R_8$, or $R'_7$ with $R'_8$ can form together a saturated 5- or 6-membered heterocycle, $Z_3$ is a cationic group of the following formula (VII)

$$—(B)_{n'''}\text{–D} \qquad (VII)$$

wherein:
B is chosen from linear and branched hydrocarbonaceous chains comprising from 1 to 15 carbon atoms, which can form at least one optionally aromatic 3- to 7-membered ring, and at least one carbon atom of the hydrocarbonaceous chain can be replaced by at least on entity chosen from oxygen, nitrogen and sulfur atoms and an $SO_2$ group, with the exception of the carbon atom connected to the nitrogen atom; wherein B does not comprise a peroxide bond or a diazo, nitro or nitroso radical,
the radical B is connected to D by any of the atoms of the radical D,
n''' is 0 or 1,
D is a cationic group chosen from the cationic groups of the following formulae (VIII) and (IX):

(VIII)

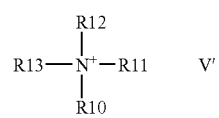
(IX)

wherein:
p is 0 or 1;
$T_1$, $T_2$, $T_3$ and $T_4$, which may be identical or different, are each chosen from an oxygen atom; a sulfur atom; a nitrogen atom which is optionally substituted with at least one radical $R_{14}$; and a carbon atom which is optionally substituted with one or two identical or different radicals $R_{14}$;
$T_5$ is chosen from a nitrogen atom and a carbon atom which is optionally substituted with at least one radical $R_{14}$;
$T_6$ is chosen from linear and branched hydrocarbonaceous chains comprising from 1 to 10 carbon atoms, which are optionally aromatic, and at least one carbon atom of the hydrocarbonaceous chain can be replaced by at least one entity chosen from oxygen, nitrogen, halogen, and sulfur atoms and an $SO_2$ group; wherein $T_6$ does not comprise a peroxide and or a diazo, nitro or nitroso radical;

T₁ or T₅ can optionally form with T₆ a 5- to 7-membered saturated or unsaturated ring, wherein each member of the ring is optionally substituted with one or two identical or different radicals $R_{14}$;

two of the adjacent radicals $T_1$, $T_2$, $T_3$, $T_4$ and $T_5$ can optionally form a 5- to 7-membered ring, wherein each member of the ring is chosen from a carbon atom which is optionally substituted with one or two identical or different radicals $R_{14}$, a nitrogen atom which is optionally substituted with at least one radical $R_{14}$, an oxygen atom, and a sulfur atom;

$R_{10}$, $R_{11}$, $R_{12}$, $R_{13}$ and $R_{14}$, which may be identical or different, are each chosen from a hydrogen atom and linear and branched hydrocarbonaceous chains comprising from 1 to 10 carbon atoms, which are optionally aromatic, and wherein at least one carbon atom of the hydrocarbonaceous chain can be replaced by at least one entity chosen from oxygen, nitrogen, halogen, and sulfur atoms and an $SO_2$ group, and/or can be substitute by, independently of one another, at least one halogen atom; wherein at least one of $R_{10}$, $R_{11}$, $R_{12}$, $R_{13}$ and $R_{14}$ does not comprise a peroxide bond or a diazo, nitro or nitroso radical;

$R_{10}$, $R_{11}$ and $R_{12}$ can also form, in pairs with the quaternary nitrogen atom to which they are attached, at least one ring chosen from 5- to 7-membered saturated rings, wherein each member of the ring is chosen from a carbon atom which is optionally substituted with one or two identical or different radicals $R_{14}$, a nitrogen atom which is optionally substituted with at least one radical $R_{14}$, an oxygen atom, and a sulfur atom, when n'''=0, then the group of formula (IX) can be connected to the compound of formula (V) and (VI) directly by the nitrogen atom of the quaternary ammonium, wherein $R_{13}$ is a single bond, and V' is an organic or inorganic anion, $Z_2$ is chosen from linear and branched $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group, wherein the radical $Z_2$ does not comprise a peroxide bond or a diazo, nitro or nitroso radical; with a proviso that $Z_2$ is not cationic when $R_7$, $R_9$, $R'_7$ or $R'_9$ is cationic, $A_2$ is a radical of formula (X) chosen from carbonaceous aromatic, pyridine and pyridazine radicals substituted with at least one radical chosen from 5-membered cationic heteroaromatic radicals, optionally substituted with at least one noncationic radical $R_{19}$ chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein $R_{19}$ does not comprise a peroxide bond or a diazo, nitro or nitroso radical; or a radical of formula (XI):

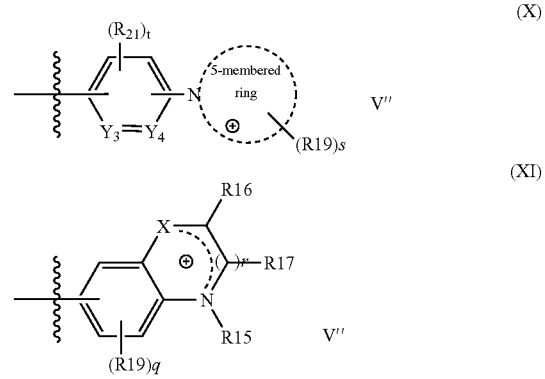

wherein:
r is equal to 0 or 1,
q is equal to 0, 1, 2 or 3,
s is equal to 0, 1, 2, 3, 4 or 5,
t is equal to 0, 1 or 2,
$Y_3$=$Y_4$ is C=C, C=N or N=N,
if r=0, then X is O, S, $NR_{18}$, $CR_{20}$,
if r=1, then X is $CR_{20}$, $R_{15}$ and $R_{18}$, which may be identical or different, are each chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen, halogen and sulfur atoms and an $SO_2$ group, with the exception of the carbon atom connected to the nitrogen atom; wherein at least one of the radicals $R_{15}$, and $R_{18}$ does not comprise a peroxide bond or a diazo, nitro or nitroso radical, $R_{16}$, $R_{17}$, $R_{19}$, $R_{20}$ and $R_{21}$, which may be identical or different, are each chosen from a hydrogen atom and linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and $SO_2$ group; wherein at least one of the radicals $R_{16}$, $R_{17}$, $R_{19}$, $R_{20}$, and $R_{21}$ does not comprise a peroxide bond or a diazo, nitro or nitroso radical, and V'' is an organic or inorganic anion, provided that in formula (I), one of the groups $A_1$, $Z_2$ and $A_3$ is a cationic group.

32. The process according to claim 31, wherein the dyeing composition comprises at least one oxidizing agent.

33. The process according to claim 31, wherein the at least one oxidizing agent is mixed with the dyeing composition at the time of application.

34. The process according to claim 32, wherein the at least one oxidizing agent is applied to the keratinous fibers in the form of an oxidizing composition simultaneously with or sequentially to the dyeing composition.

35. The process according to claim 31, wherein the dyeing composition further at comprises least one oxidation base and optionally at least one coupler, and the application of the dyeing composition to the keratinous fibers is carried out in the presence of at least one oxidizing agent.

36. The process according to claim 35, wherein the at least one oxidizing agent is mixed with the dyeing composition at the time of application.

37. The process according to claim 35, wherein the at least one oxidizing agent is applied to the keratinous fibers in the form of an oxidizing composition simultaneously with or sequentially to the dyeing composition.

38. The process according to claim 31, wherein the keratinous fibers are hair.

39. A multi-compartment device, comprising a first compartment comprising a dyeing composition comprising at least one dicationic monoazo dye chosen from compounds of the following formulae (I) and (II):

wherein:

n is equal to 0 or 1, $Z_1$ is a 5- or 6-membered cationic heteroaromatic radical chosen from radicals of formulae (III) and (IV):

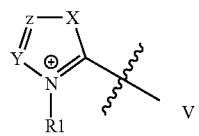

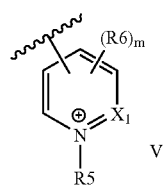

wherein:

X is $NR_3$, S or O, Z is $CR_2$ or N, and Y is $CR_4$ or N, with the proviso that:

when X is $NR_3$ or O and Z is $CR_2$, then Y is $CR_4$; or N, when X is S, then Z is N or Y is N, when X is S and Z is N, then Y is $CR_4$, $X_1$ is $CR_6$ or N, m is equal to 0, 1, 2 or 3, $R_1$, $R_3$ and $R_5$, which may be identical or different, are each chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen, halogen and sulfur atoms and an $SO_2$ group, with the exception of the carbon atom connected to the nitrogen atom of the ring of formula (III) or (IV); wherein at least one of $R_1$, $R_3$ and $R_5$ does not comprise a peroxide bond or a diazo, nitro or nitroso radical;

$R_2$, $R_4$ and $R_6$, which may be identical or different, are each chosen from a hydrogen atom and linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein at least one of the radicals $R_2$, $R_4$ and $R_6$ does not comprise a peroxide bond or a diazo, nitro or nitroso radical; the radicals $R_2$ and $R_4$ can form together a carbonaceous aromatic ring, and V is an organic or inorganic anion, $A_1$ and $A_3$, which may be identical or different, are each chosen from divalent radicals of formulae (V) and (VI)

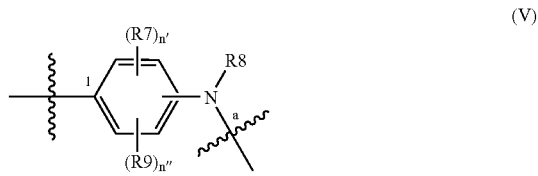

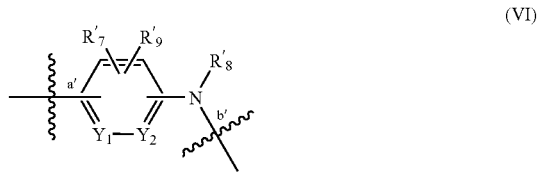

wherein n' is equal to 0, 1, 2 or 3, n" is equal to 0 or 1, $Y_1$–$Y_2$ is C—N or N—N, when n=0, then the bond a of the group $A_1$ of formula (V) is connected to the functional group $Z_2$ of formula (I) or, when n=0, then the bond b' of the group $A_1$ of formula (VI) is connected to the functional group $Z_2$ of formula (I), when n=1, then the bond a of the group $A_1$ of formula (V) is connected to the $C_1$ of the group $A_3$ of formula (V), the bond a of the group $A_3$ of formula (V) being connected to the functional group $Z_2$ of formula (I) or, when n=1, then the bond a of the group $A_1$ of formula (V) is connected to the carbon carrying the bond a' of the group $A_3$ of formula (VI), the bond b' being connected to the functional group $Z_2$ of formula (I), when n=1, then the bond b' of the group $A_1$ of formula (VI) is connected to the $C_1$ carbon of the group $A_3$ of formula (V), the bond a being connected to the functional group $Z_2$ of formula (I) or, when n=1, then the bond b' of the group $A_1$ of formula (VI) is connected to the carbon carrying the bond a' of the group $A_3$ of formula (VI), the bond b' of the group $A_3$ of formula (VI) being connected to the functional group $Z_2$ of formula (I), $R_8$ and $R'_8$, which may be identical or different, are each a noncationic group chosen from a hydrogen atom and linear and branched $C_1$–$C_{10}$ hydrocarbonaceous chains which can form an optionally aromatic 5- to 7-membered carbon ring; it being possible for at least one carbon atom of the hydrocarbonaceous chain to be replaced by at least one entity chosen from oxygen, nitrogen and sulfur atoms and an $SO_2$ group with the exception of the carbon atom connected to the nitrogen atom; wherein at least one of the radicals $R_8$ and $R'_8$ does not comprise a peroxide bond or a diazo, nitro or nitroso radical;

$R_7$, $R_9$, $R'_7$ and $R'_9$, which may be identical or different, are each a cationic group $Z_3$ or a noncationic group chosen from a hydrogen atom and linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein the noncationic group does not comprise a peroxide bond or a diazo, nitro or nitroso radical, provided that only one of the groups $R_7$, $R_9$, $R'_7$ and $R'_9$ is cationic, $R_7$ with $R_8$, or $R'_7$ with $R'_8$ can form together a saturated 5- or 6-membered heterocycle, $Z_3$ is a cationic group of the following formula (VII)

$$—(B)_{n'''}.D \qquad (VII)$$

wherein:

B is chosen from linear and branched hydrocarbonaceous chains comprising from 1 to 15 carbon atoms, which can form at least one optionally aromatic 3- to 7-membered ring, and at least one carbon atom of the hydrocarbonaceous chain can be replaced by at least one entity chosen from oxygen, nitrogen and sulfur atoms and an $SO_2$ group, with the exception of the carbon atom connected to the nitrogen atom; wherein B does not comprise a peroxide bond or a diazo, nitro or nitroso radical, the radical B is connected to D by any of the atoms of the radical D, n''' is 0 or 1, D is a cationic group chosen from the cationic groups of the following formulae (VIII) and (IX):

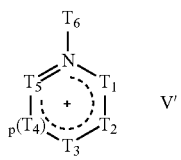

(VIII)

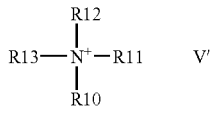

(IX)

wherein:

p is 0 or 1;

$T_1$, $T_2$, $T_3$ and $T_4$, which may be identical or different, are each chosen from an oxygen atom; a sulfur atom; a nitrogen atom which is optionally substituted with at least one radical $R_{14}$; and a carbon atom which is optionally substituted with one or two identical or different radicals $R_{14}$;

$T_5$ is chosen from a nitrogen atom and a carbon atom which is optionally substituted with at least one radical $R_{14}$;

$T_6$ is chosen from linear and branched hydrocarbonaceous chains comprising from 1 to 10 carbon atoms, which are optionally aromatic, and at least one carbon atom of the hydrocarbonaceous chain can be replaced by at least one entity chosen from oxygen, nitrogen, halogen, and sulfur atoms and an $SO_2$ group; wherein $T_6$ does not comprise a peroxide bond or a diazo, nitro or nitroso radical;

$T_1$ or $T_5$ can optionally form with $T_6$ a 5- to 7-membered saturated or unsaturated ring, wherein each member of the ring is optionally substituted with one or two identical or different radicals $R_{14}$;

two of the adjacent radicals $T_1$, $T_2$, $T_3$, $T_4$ and $T_5$ can optionally form a 5- to 7-membered ring, wherein each member of the ring is chosen from a carbon atom which is optionally substituted with one or two identical or different radicals $R_{14}$, a nitrogen atom which is optionally substituted with at least one radical $R_{14}$, an oxygen atom, and a sulfur atom;

$R_{10}$, $R_{11}$, $R_{12}$, $R_{13}$ and $R_{14}$, which may be identical or different, are each chosen from a hydrogen atom and linear and branched hydrocarbonaceous chains comprising from 1 to 10 carbon atoms, which are optionally aromatic, and wherein at least one carbon atom of the hydrocarbonaceous chain can be replaced by at least one entity chosen from oxygen, nitrogen, halogen, and sulfur atoms and an $SO_2$ group, and/or can be substituted by, independently of one another, at least one halogen atom; wherein at least one of $R_{10}$, $R_{11}$, $R_{12}$, $R_{13}$ and $R_{14}$ does not comprise a peroxide bond or a diazo, nitro or nitroso radical;

$R_{10}$, $R_{11}$, and $R_{12}$ can also form, in pairs with the quaternary nitrogen atom to which they are attached, at least one ring chosen from 5- to 7-membered saturated rings, wherein each member of the ring is chosen from a carbon atom which is optionally substituted with one or two identical or different radicals $R_{14}$, a nitrogen atom which is optionally substituted with at least one radical $R_{14}$, an oxygen atom, and a sulfur atom, when n'''=0, then the group of formula (IX) can be connected to the compound of formula (V) an (VI) directly by the nitrogen atom of the quaternary ammonium, wherein $R_{13}$ is a single bond, and V' is an organic or inorganic anion, $Z_2$ is chosen from linear and branched $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group, wherein the radical $Z_2$ does not comprise a peroxide bond or a diazo, nitro or nitroso radical; with a proviso that $Z_2$ is not cationic when $R_7$, $R_9$, $R'_7$ or $R'_9$ is cationic, $A_2$ is a radical of formula (X) chosen from carbonaceous aromatic, pyridine and pyridazine radicals substituted with at least one radical chosen from 5-membered cationic heteroaromatic radicals, optionally substituted with at least one noncationic radical $R_{19}$ chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein $R_{19}$ does not comprise a peroxide bond or a diazo, nitro or nitroso radical; or a radical of formula (XI):

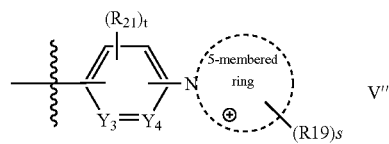

(X)

-continued

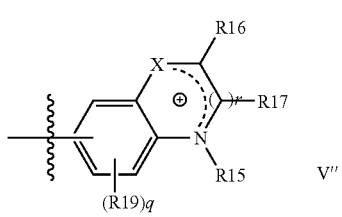
(XI)

wherein:
r is equal to 0 or 1,
q is equal to 0, 1, 2 or 3,
s is equal to 0, 1, 2, 3, 4 or 5,
t is equal to 0, 1 or 2,
$Y_3\!=\!Y_4$ is C=C, C=N or N=N,
if r=0, then X is O, S, $NR_{18}$, $CR_{20}$,
if r=1, then X is $CR_{20}$,
$R_{15}$ and $R_{18}$, which may be identical or different, are each chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen, halogen and sulfur atoms and an $SO_2$ group, with the exception of the carbon atom connected to the nitrogen atom; wherein at least one of the radicals $R_{15}$, and $R_{18}$ does not comprise a peroxide bond or a diazo, nitro or nitroso radical,
$R_{16}$, $R_{17}$, $R_{19}$, $R_{20}$ and $R_{21}$, which may be identical or different, are each chosen from a hydrogen atom and linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein at least one of the radicals $R_{16}$, $R_{17}$, $R_{19}$, $R_{20}$, and $R_{21}$ does not comprise a peroxide bond or a diazo, nitro or nitroso radical, and
V″ is an organic or inorganic anion, provided that in formula (I), one of the groups $A_1$, $Z_2$ and $A_3$ is a cationic group, and
a second compartment comprising an oxidizing composition.

40. A dicationic monoazo compound, chosen from compounds of formulae (I) and (II):

(I)

(II)

wherein:
n is equal to 0 or 1,
$Z_1$ is a 5- or 6-membered cationic heteroaromatic radical chosen from radicals of formulae (III) and (IV):

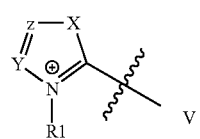
(III)

-continued

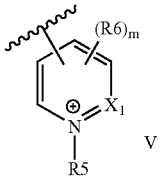
(IV)

wherein:
X is $NR_3$, S or O, Z is $CR_2$ or N, and Y is $CR_4$ or N, with the proviso that:
when X is $NR_3$ or O and Z is $CR_2$, then Y is $CR_4$ or N,
when X is S, then Z is N or Y is N,
when X is S and Z is N, then Y is $CR_4$,
$X_1$ is $CR_6$ or N,
m is equal to 0, 1, 2 or 3,
$R_1$, $R_3$ and $R_5$, which may be identical or different, are each chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen, halogen and sulfur atoms and an $SO_2$ group, with the exception of the carbon atom connected to the nitrogen atom of the ring of formula (III) or (IV); wherein at least one of $R_1$, $R_3$ and $R_5$ does not comprise a peroxide bond or a diazo, nitro or nitroso radical;
$R_2$, $R_4$ and $R_6$, which may be identical or different, are each chosen from a hydrogen atom and linear an branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein at least one of the radicals $R_2$, $R_4$ and $R_6$ does not comprise a peroxide bond or a diazo, nitro or nitroso radical; the radicals $R_2$ and $R_4$ can form together a carbonaceous aromatic ring, and
V is an organic or inorganic anion,
$A_1$ and $A_3$, which may be identical or different, are each chosen from divalent radicals of formulae (V) and (VI)

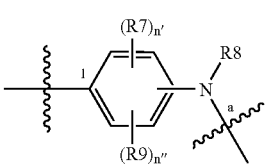
(V)

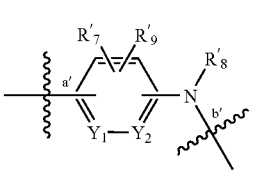
(VI)

wherein
n' is equal to 0, 1, 2 or 3,
n″ is equal to 0 or 1, $Y_1$–$Y_2$ is C—N or —N, when n=0, then the bond a of the group $A_1$ of formula (V) is connected to the functional group $Z_2$ of formula (I) or, when n=0, then the bond b' of the group $A_1$ of formula (VI) is connected to the functional group $Z_2$ of formula (I), when n=1, then the bond a of the group $A_1$ of formula (V) is connected to the $C_1$ of the group $A_3$ of formula (V), the bond a of the group $A_3$ of formula (V) being connected to the functional group $Z_2$ of formula (I) or, when n=1, then the bond a of the group $A_1$ of formula (V) is connected to the carbon carrying the bond a' of the group $A_3$ of formula (VI), the bond b' being connected to the functional group $Z_2$ of formula (I), when n=1, then the bond b' of the group $A_1$ of formula (VI) is connected to the $C_1$ carbon of the group $A_3$ of formula (V), the bond a being connected to the functional group $Z_2$ of formula (I) or, when n=1, then the bond b' of the group $A_1$ of formula (VI) is connected to the carbon carrying the bond a' of the group $A_3$ of formula (VI), the bond b' of the group $A_3$ of formula (VI) being connected to the functional group $Z_2$ of formula (I), $R_8$ is a hydrogen atom $R'_8$ is a noncationic group chosen from a hydrogen atom and linear and branched $C_1$–$C_{10}$ hydrocarbonaceous chains which can form an optionally aromatic 5- to 7-membered carbon ring; it being possible for at least one carbon atom of the hydrocarbonaceous chain to be replaced by at least one entity chosen from oxygen, nitrogen and sulfur atoms and an $SO_2$ group with the exception of the carbon atom connected to the nitrogen atom; wherein $R'_8$ does not comprise a peroxide bond or a diazo, nitro or nitroso radical;

$R_7$, $R_9$, $R'_7$ and $R'_9$, which may be identical or different, are each a cationic group $Z_3$ or a noncationic group chosen from a hydrogen atom and linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein the noncationic group does not comprise a peroxide bond or a diazo, nitro or nitroso radical, provided that only one of the groups $R_7$, $R_9$, $R'_7$ and $R'_9$ is cationic, $R_7$ with $R'_8$ can form together a saturated 5- or 6-membered heterocycle, $Z_3$ is a cationic group of the following formula (VII)

$$—(B)_{n'''}—D \quad (VII)$$

wherein:

B is chosen from linear and branched hydrocarbonaceous chains comprising from 1 to 15 carbon atoms, which can form at least one optionally aromatic 3- to 7-membered ring, and at least one carbon atom of the hydrocarbonaceous chain can be replaced by at least one entity chosen from oxygen, nitrogen and sulfur atoms and an $SO_2$ group, with the exception of the carbon atom connected to the nitrogen atom; wherein B does not comprise a peroxide bond or a diazo, nitro or nitroso radical, the radical B is connected to D by any of the atoms of the radical D, n''' is 0 or 1, D is a cationic group chosen from the cationic groups of the following formulae (VIII) and (IX):

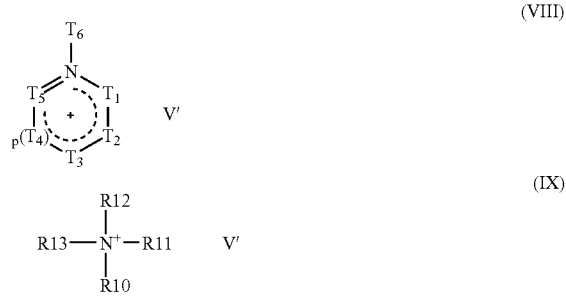

wherein:

p is 0 or 1;

$T_1$, $T_2$, $T_3$ and $T_4$, which may be identical or different, are each chosen from an oxygen atom; a sulfur atom; a nitrogen atom which is optionally substituted with at least one radical $R_{14}$; and a carbon atom which is optionally substituted with one or two identical or different radicals $R_{14}$;

$T_5$ is chosen from a nitrogen atom and a carbon atom which is optionally substituted with at least one radical $R_{14}$;

$T_8$ is chosen from linear and branched hydrocarbonaceous chains comprising from 1 to 10 carbon atoms, which are optionally aromatic, and at least one carbon atom of the hydrocarbonaceous chain can be replaced by at least one entity chosen from oxygen, nitrogen, halogen, and sulfur atoms and an $SO_2$ group; wherein $T_6$ does not comprise a peroxide bond or a diazo, nitro or nitroso radical;

$T_1$ or $T_5$ can optionally form with $T_6$ a 5- to 7-membered saturated or unsaturated ring, wherein each member of the ring is optionally substituted with one or two identical or different radicals $R_{14}$;

two of the adjacent radicals $T_1$, $T_2$, $T_3$, $T_4$ and $T_5$ can optionally form a 5- to 7-membered ring, wherein each member of the ring is chosen from a carbon atom which is optionally substituted with one or two identical or different radicals $R_{14}$, a nitrogen atom which is a optionally substituted with at least one radical $R_{14}$, an oxygen atom, and a sulfur atom;

$R_{10}$, $R_{11}$, $R_{12}$, $R_{13}$ and $R_{14}$, which may be identical or different, are each chosen from a hydrogen atom and linear and branched hydrocarbonaceous chains comprising from 1 to 10 carbon atoms, which are optionally aromatic, and wherein at least one carbon atom of the hydrocarbonaceous chain can be replaced by at least one entity chosen from oxygen, nitrogen, halogen, and sulfur atoms and an $SO_2$ group, and/or can be substituted by, independently of one another, at least one halogen atom; wherein at least one of $R_{10}$, $R_{11}$, $R_{12}$, $R_{13}$ and $R_{14}$ does not comprise a peroxide bond or a diazo, nitro or nitroso radical;

$R_{10}$, $R_{11}$ and $R_{12}$ can also form, in pairs with the quaternary nitrogen atom to which they are attached, at least one ring chosen from 5- to 7-membered saturated rings, wherein each member of the ring is chosen from a carbon atom which is optionally substituted with one or two identical or different radicals $R_{14}$, a nitrogen atom which is optionally substituted with at least one radical $R_{14}$, an oxygen atom, and a sulfur atom, when $n'''=0$, then the group of formula (IX) can be connected to the compound of formula (V) an (VI) directly by the nitrogen atom of the quaternary ammonium, wherein $R_{13}$ is a single bond, and V' is an organic or inorganic anion, $Z_2$ is chosen from linear and branched $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group, wherein the radical $Z_2$ does not comprise a peroxide bond or a diazo, nitro or nitroso radical; with a proviso that $Z_2$ is not cationic when $R_7$, $R_9$, $R'_7$ or $R'_9$ is cationic, $A_2$ is a radical of formula (X) chosen from carbonaceous aromatic, pyridine and pyridazine radicals substituted with at least one radical chosen from 5-membered cationic heteroaromatic radicals optionally substituted with at least one noncationic radical $R_{19}$ chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and an $SO_2$ group; wherein $R_{19}$ does not comprise a peroxide bond or a diazo, nitro or nitroso radical; or a radical of formula (XI):

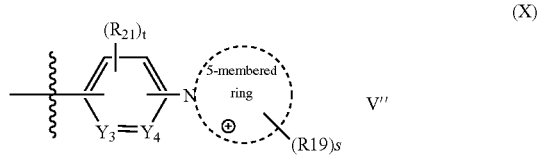
(X)

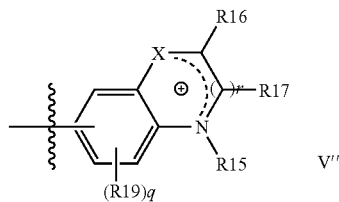
(XI)

wherein:
r is equal to 0 or 1,
q is equal to 0, 1, 2 or 3,
s is equal to 0, 1, 2, 3, 4 or 5,
t is equal to 0, or 2,
$Y_3=Y_4$ is C=C, C=N or N=N,
if r=0, then X is O, S, $NR_{18}$, $CR_{20}$,
if r=1, then X is $CR_{20}$,
$R_{15}$ and $R_{18}$, which may be identical or different, are each chosen from linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen, halogen and sulfur atoms and an $SO_2$ group, with the exception of the carbon atom connected to the nitrogen atom; wherein at least one of the radicals $R_{15}$, an $R_{18}$ does not comprise a peroxide bond or a diazo, nitro or nitroso radical, $R_{16}$, $R_{17}$, $R_{19}$, $R_{20}$ and $R_{21}$, which may be identical or different, are each chosen from a hydrogen atom and linear and branched, saturated and unsaturated $C_1$–$C_{10}$ hydrocarbonaceous chains which can form an optionally aromatic 5- to 7-membered carbonaceous ring; it being possible for at least one carbon atom of the hydrocarbonaceous chain to be replaced by at least one entity chosen from oxygen, nitrogen and sulfur atoms and a $SO_2$ group; wherein at least one of the radicals $R_{16}$, $R_{17}$, $R_{19}$, $R_{20}$, and $R_{21}$ does not comprise a peroxide bond or a diazo, nitro or nitroso radical, and V''' is an organic or inorganic anion,
provided that in formula (I), one of the groups $A_1$, $Z_2$ and $A_3$ is a cationic group.

* * * * *

UNITED STATES PATENT AND TRADEMARK OFFICE
CERTIFICATE OF CORRECTION

PATENT NO. : 7,060,110 B2
APPLICATION NO. : 10/473810
DATED : June 13, 2006
INVENTOR(S) : Laurent Vidal et al.

It is certified that error appears in the above-identified patent and that said Letters Patent is hereby corrected as shown below:

On the title page, item (57), line 2, "dying" should read --dyeing--.

Claim 1, col. 57, line 64, "bond b'" should read --bond a'--.

Claim 1, col. 57, line 65, "bond a'" should read --bond b'--.

Claim 1, col. 58, line 29, "-$(B)_{n'''}D$" should read -- $(B)_{n'''}$-D--.

Claim 1, col. 59, line 48, "formula (V)" should read --formulae (V)--.

Claim 1, col. 60, line 44, "$R_{15}$, and" should read --$R_{15}$ and--.

Claim 8, col. 61, line 61, "$(CH_2)_p$-Tr-$(CH_2)_q$-$V_1R'$" should read --$(CH_2)_p$-T-$(CH_2)_q$-$V_1R'$--.

Claim 8, col. 61, line 65, "N" wherein" should read --NR" wherein--.

Claim 11, col. 62, lines 21-22, "$(CH_2)_p$-Tr-$(CH_2)_q$-$V_1R'$" should read --$(CH_2)_p$-T-$(CH_2)_q$-$V_1R'$--.

Claim 31, col. 103, line 31, "or -N," should read --or N-N,--.

Claim 31, col. 104, line 67, "peroxide and or" should read --peroxide bond or--.

Claim 31, col. 105, line 23, "substitute" should read --substituted--.

Claim 31, col. 105, line 39, "formula (V)" should read --formulae (V)--.

Claim 31, col. 106, line 35, "$R_{15}$, and" should read --$R_{15}$ and--.

Claim 31, col. 106, line 44, "and $SO_2$" should read --and an $SO_2$--.

Claim 35, col. 106, line 61, "at comprises" should read --comprises at--.

Claim 39, col. 107, line 38, "$CR_4$; or" should read --$CR_4$ or--.

Claim 39, col. 110, line 21, "an d" should read --and--.

Claim 39, col. 110, line 31, "formula (V)" should read --formule (V)--.

UNITED STATES PATENT AND TRADEMARK OFFICE
CERTIFICATE OF CORRECTION

PATENT NO. : 7,060,110 B2
APPLICATION NO. : 10/473810
DATED : June 13, 2006
INVENTOR(S) : Laurent Vidal et al.

It is certified that error appears in the above-identified patent and that said Letters Patent is hereby corrected as shown below:

Claim 39, col. 110, line 31, "an (VI)" should read --and (VI)--.

Claim 39, col. 111, line 30, "$R_{15}$, and" should read --$R_{15}$ and--.

Claim 40, col. 112, line 34, "an" should read --and--.

Claim 40, col. 113, line 1, "or -N" should read --or N-N,--.

Claim 40, col. 114, line 27, "$T_8$ is" should read --$T_6$ is--.

Claim 40, col. 114, line 48, "$_{R12}$," should read --$R_{12}$,--.

Claim 40, col. 115, line 4, "formula (V)" should read --formulae (V)--.

Claim 40, col. 115, line 4, "an (VI)" should read --and (VI)--.

Claim 40, col. 116, line 15, "0, or 2," should read --0, 1 or 2,--.

Claim 40, col. 116, line 28, "$R_{15}$," should read --$R_{15}$--.

Claim 40, col. 116, line 28, "an" should read --and--.

Claim 40, col. 116, line 37, "a $SO_2$" should read --an $SO_2$--.

Signed and Sealed this

Thirtieth Day of January, 2007

JON W. DUDAS
*Director of the United States Patent and Trademark Office*